US010894851B2

(12) United States Patent
Dyson et al.

(10) Patent No.: US 10,894,851 B2
(45) Date of Patent: Jan. 19, 2021

(54) IONIC POLYMERS AND USE THEREOF IN PROCESSING OF BIOMASS

(71) Applicant: ECOLE POLYTECHNIQUE FEDERALE DE LAUSANNE (EPFL), Lausanne (CH)

(72) Inventors: Paul Dyson, Ecublens (CH); Zhaofu Fei, Kaiseraugst (CH); Sviatlana Siankevich, Chavannes-Renens (CH); Georgios Savoglidis, Chavannes-Renens (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 213 days.

(21) Appl. No.: 16/085,809

(22) PCT Filed: Mar. 16, 2017

(86) PCT No.: PCT/EP2017/056292
§ 371 (c)(1),
(2) Date: Sep. 17, 2018

(87) PCT Pub. No.: WO2017/158117
PCT Pub. Date: Sep. 21, 2017

(65) Prior Publication Data
US 2019/0031797 A1 Jan. 31, 2019

(30) Foreign Application Priority Data
Mar. 16, 2016 (EP) .................................. 16160626

(51) Int. Cl.
*C08F 212/00* (2006.01)
*C08F 212/14* (2006.01)
*C13K 1/02* (2006.01)
*C08F 12/26* (2006.01)
*C08F 212/34* (2006.01)
(Continued)

(52) U.S. Cl.
CPC ............. *C08F 212/14* (2013.01); *B01J 31/06* (2013.01); *B01J 35/065* (2013.01); *C07C 51/487* (2013.01); *C07D 307/44* (2013.01); *C07D 307/50* (2013.01); *C08F 12/26* (2013.01); *C08F 12/30* (2013.01); *C08F 212/34* (2013.01); *C08F 236/20* (2013.01); *C13K 1/02* (2013.01); *C13K 13/00* (2013.01); *D21C 3/20* (2013.01);
(Continued)

(58) Field of Classification Search
None
See application file for complete search history.

(56) References Cited

U.S. PATENT DOCUMENTS 8,575,374 B1 11/2013 DeLong et al.
2010/0319862 A1 12/2010 Rahman
2016/0032038 A1* 2/2016 Baynes ................. C08L 97/005
127/29

OTHER PUBLICATIONS

Liu et al. "Depolymerization of crystalline cellulose catalyzed by acidic ionic liquids grafted onto sponge-like nanoporous polymers". Chem. Commun., vol. 49, pp. 8456-8458, 2013.
(Continued)

*Primary Examiner* — Stefanie J Cohen
(74) *Attorney, Agent, or Firm* — Oliff PLC

(57) ABSTRACT

Ionic polymers (IP) are made of anions and a polymeric backbone containing cations. The ionic polymers are incorporated in membranes or attached to solid supports and use of the ionic polymers in processing of biomass.

15 Claims, 5 Drawing Sheets

(51) Int. Cl.
*D21C 5/00* (2006.01)
*C08F 12/30* (2006.01)
*D21C 3/22* (2006.01)
*D21C 3/20* (2006.01)
*C13K 13/00* (2006.01)
*D21C 11/00* (2006.01)
*B01J 31/06* (2006.01)
*B01J 35/06* (2006.01)
*C07C 51/487* (2006.01)
*C07D 307/44* (2006.01)
*C07D 307/50* (2006.01)
*C08F 236/20* (2006.01)

(52) U.S. Cl.
CPC ............... *D21C 3/222* (2013.01); *D21C 5/00* (2013.01); *D21C 11/0007* (2013.01)

(56) References Cited

OTHER PUBLICATIONS

May 4, 2017 Search Report issued in International Patent Application No. PCT/EP2017/056292.
May 4, 2017 Written Opinion issued in International Patent Application No. PCT/EP2017/056292.

* cited by examiner

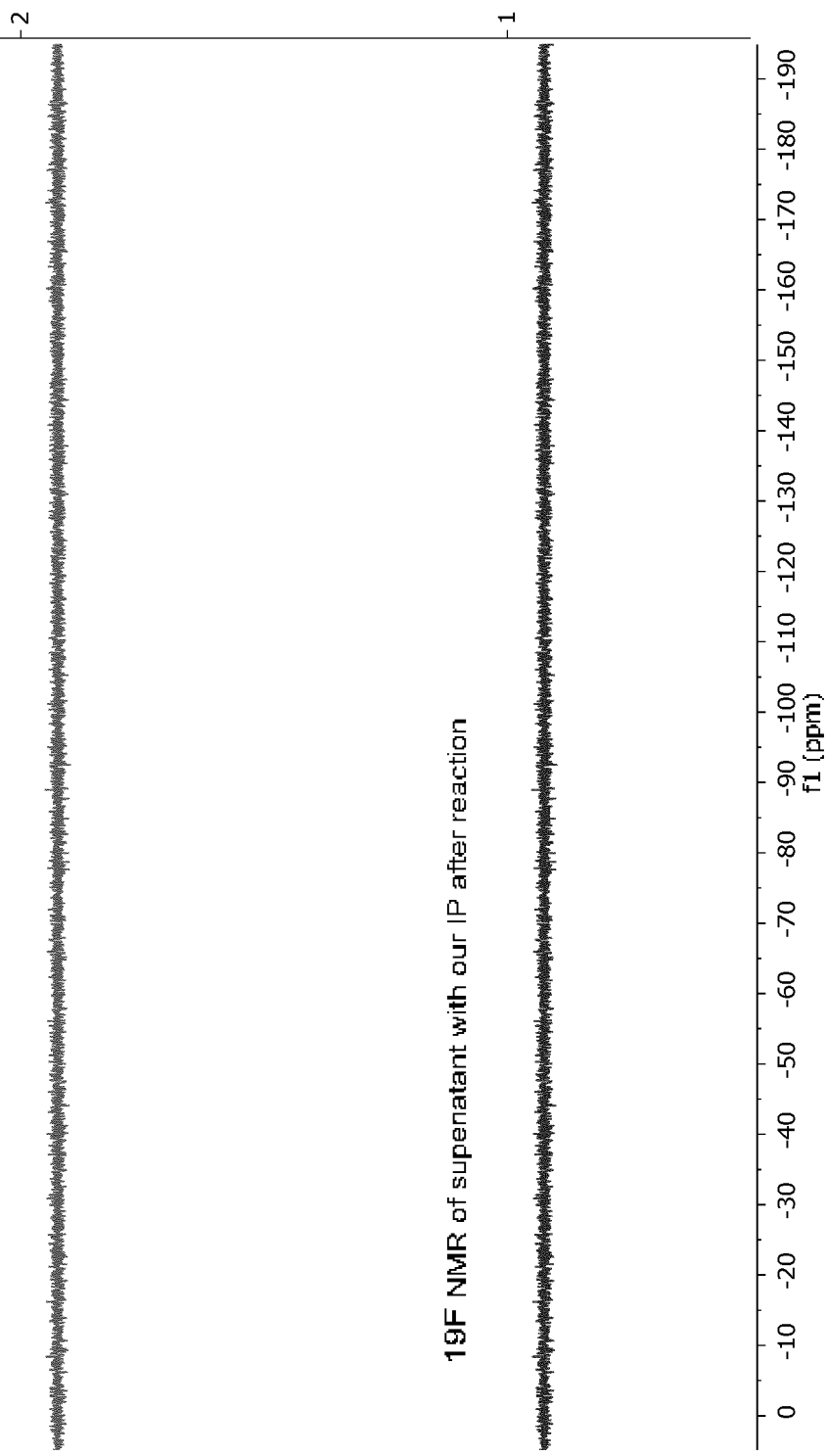
Figure 2 – cont.

IONIC POLYMERS AND USE THEREOF IN PROCESSING OF BIOMASS

FIELD OF THE INVENTION

The invention provides ionic polymers (IP) consisting of anions and a polymeric backbone containing cations. The invention also provides the ionic polymers incorporated in membranes or attached to solid supports and use of the ionic polymers in processing of biomass.

BACKGROUND OF THE INVENTION

The depletion of fossil fuels, the impact on the environment from carbon positive processes, and the increase in waste from industrialization represent major hurdles for future industrial development. In recent years, the concept of shifting towards integrated biorefineries as alternatives to classical petrochemical refineries for the production of fuels and platform chemicals is gaining momentum. A biorefinery uses lignocellulosic biomass instead of fossil fuels to develop the same products as a petrochemical refinery with a substantially smaller environmental impact.

Lignocellulosic biomass (or simply biomass) is comprised primarily of cellulose, hemicellulose and lignin, large polymeric structures that can be broken down to simple constituents, which can be further used as a feedstock for chemical or biological transformations. As a result, the fragmentation of biomass into simple constituents results in mixtures rich in C5 and C6 sugars, lipids, proteins, phenols and inorganics salts. Hence, biomass can be viewed as an excellent source for valuable compounds. A biorefinery that utilizes biomass as a carbon source has the added benefit of utilization of waste with a positive environmental and social impact. Therefore, efficient technologies to decompose biomass to simple constituents and extract the valuable components is critical for the implementation and successful operation of a biorefinery.

Two hydrolysis methods are commonly used to extract sugars from biomass: acidic hydrolysis and enzymatic hydrolysis. Acidic hydrolysis is performed with dilute or concentrated acids, however, dilute acids require high temperatures and pressures whereas concentrated acids must be removed from the product before further processing can occur. Enzymatic processes require a stable supply of enzymes and pretreatment to facilitate the hydrolysis of cellulose and hemicellulose, especially in the case of extraction from lignocellulosic materials. Moreover, in the case of lignocellulose treatment with enzymes, the pH and temperature must be precisely regulated and the lignin must be separated or removed prior to cellulose and hemicellulose conversion, adding extra steps to the biomass pretreatment phase. Current methods thus use a pretreatment of the cellulose before processing to break up some of the crystalline regions increasing the percentage of amorphous regions in the cellulose; this, in turn, speeds up the depolymerization to glucose and improves the overall product yield. There are several pretreatment methods, such as biological, physical, chemical, and physiochemical. However, these methods of pretreatment are expensive, because they use costly solvents, are energy intensive, or are time consuming.

As alternatives to conventional mineral acid hydrolysis several other approaches exist such as the application of solid acid catalysts, which is seen to be more environmentally friendly as they simplify downstream processing. For instance, sulfonic acid ($-SO_3H$) functionalized solid catalysts exhibit highly efficient catalytic performance for cellulose hydrolysis and show different catalytic effects depending on the morphology of the support.

As further alternatives, ionic liquids (ILs) have been utilized in the processing of biomass either as a pretreatment for traditional methods or as a solvent for cellulose which is then reacted with enzymes. Ionic liquid based pretreatments have shown potential as cost effective alternatives to aqueous based pretreatments in both enzymatic hydrolysis as well as acid hydrolysis. The studies demonstrated the benefits of using an ionic liquid in the hydrolysis of cellulose. The dissolution of the cellulose allows for increased reaction rates due to the accessibility of the glucosidic bonds in the cellulose. One of the drawbacks to this method is the use of concentrated mineral acid, up to 98% wt. $H_2SO_4$, which requires care in handling and is volatile. Another report suggested the use of ILs, again as a solvent for cellulose, but with solid acid catalysts for the hydrolysis of cellulose. While this system demonstrated the ability to convert cellulose to simple sugars, heterogeneous catalysis can have low yields due to inefficient mixing. US 2010/0319862 A1 (The Board of Trustees of the University of Alabama) discloses methods involving multiphasic (e.g., biphasic) compositions comprising an ionic liquid (IL) and a fractionation polymer, such as a polyalkylene glycol, in the substantial absence of water for processing biomass.

Recently ILs containing acidic units have shown high performance in selectively deconstructing biomass and also in the simultaneous catalytic conversion of the constituents. For example, U.S. Pat. No. 8,575,374 B1 (DeLong et al.) discloses that the depolymerization method involves dissolving the biomass in a homogeneous solution comprising an ionic liquid solvent and an ionic liquid catalyst as a depolymerization catalyst. The depolymerization reaction rates are facilitated by heating and stirring of the ionic liquid solvent and ionic liquid catalyst solution. However, the major drawback during the hydrolysis with solid acids and/or ILs is leaching and/or difficulties in separation, which limits their application.

For the preparation of food grade and human consumption products, ionic liquid and/or other conventional catalyst contamination of products is a serious issue. Leaching of the catalyst into the product would implicate a time-consuming and costly cleaning step, which would make the whole process of preparation of food grade and human consumption products more expensive. Indeed, separation of ILs from products can be complicated and can result in increased costs in separation processes. In addition, even if a complete removal of ILs and/or other conventional catalyst is achieved, there is still a risk that such products would never qualify as food grade in certain markets due to severe food legislations. In order to facilitate the recovery of ILs from the mixture, polymers of the components of ILs or so called ionic polymers (IP) or solid supported ILs have been proposed in the literature for different applications. For example, the sponge-like polymer PDVB—$SO_3H[C_3vim]$ [$CF_3SO_3$] obtained by co-polymerization of divinylbenzene (DVB) with 1-vinylimidazole and sodium p-styrenesulfonate at 100° C., followed by reaction with 1,3-propane sultone and ion exchange with $CF_3SO_3H$ has been found to be an efficient catalyst for the deconstruction of crystalline cellulose into sugars in ILs (Fujian Liu et al., Depolymerization of crystalline cellulose catalysed by acidic ionic liquids grafted onto sponge-like nanoporous polymers, Chem. Commun., 2013, 49, 8456-8458). However, there is still possible problem of leaching.

Therefore, there is still a need for highly catalytically active ionic polymers (IPs), without leaching of their components in the medium, that are simple and safe for use in processing of biomass.

SUMMARY OF THE INVENTION

An aspect of the present invention provides an ionic polymer (IP) of formula (I) consisting of anions and a polymeric backbone containing cations

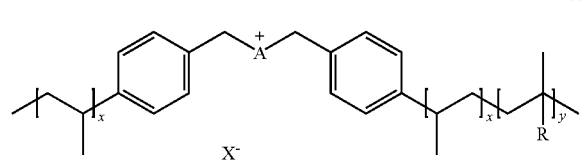

(I)

wherein
R is selected from substituted $C_1$-$C_{20}$ alkyl and substituted $C_5$-$C_{10}$ aryl, wherein substituents are selected from the group comprising H, —$SO_3H$, —COOH, —[P(=O)(OH)$_2$], —[P(=O)(OH)], —O—$SO_3H$, —O—COOH, O[P(=O)(OH)$_2$], —O—[P(=O)(OH)];
A is a cation selected from the group comprising

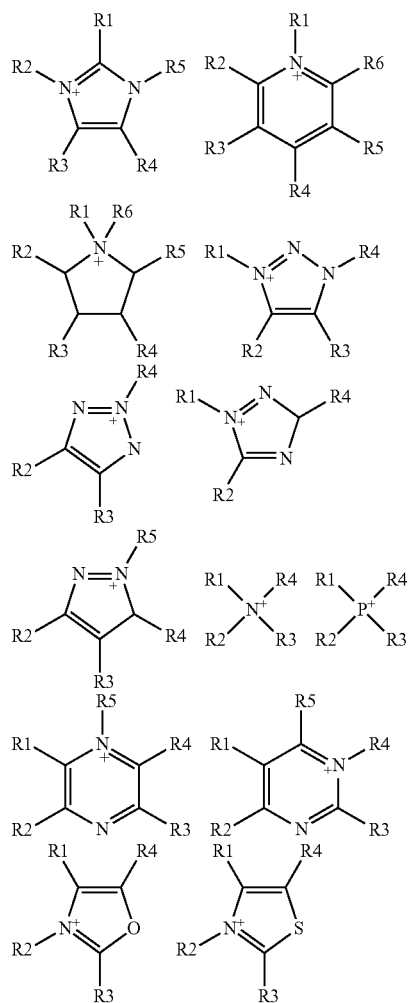

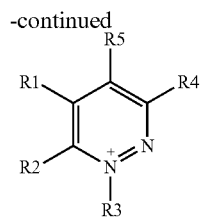

R1, R2, R3, R4, R5, R6 and R7 are each independently selected from the group comprising a bond, H, $C_1$-$C_6$ alkyl, allyl, $CH_3$—$(CH_2)n$-O—$(CH_2)m$-$CH_3$, $C_1$-$C_6$ alkoxy, $C_1$-$C_6$ alkoxyalkyl, benzyl, —$SO_3H$, provided that two of R1, R2, R3, R4, R5, R6 and R7 are each a bond to the polymeric backbone;
n and m are independently selected from 0, 1, 2, 3, 4, 5, 6;
x and y are integers each independently selected within the range 1 to 1000;
X is selected from the group comprising F$^-$, Cl$^-$, Br$^-$, I$^-$, ClO$_4^-$, BF$_4^-$, PF$_6^-$, AsF$_6^-$, SbF$_6^-$, NO$_2^-$, NO$_3^-$, HSO$_4^-$, SO$_4^{2-}$, PO$_4^{3-}$, HPO$_4^{2-}$, CF$_3$CO$_2^-$, CF$_3$CO$_3^-$, CO$_3^{2-}$, CF$_3$SO$_3^-$, $C_1$-$C_6$ carboxylate, CN$^-$, SCN$^-$, OCN$^-$, CNO$^-$, N$_3^-$, tosylate, mesylate, trifluoromethanesulfonate, trifluoroethane sulfonate, di-trifluoromethanesulfonyl amino, docusate, xylenesulfonate;

A further aspect of the present invention provides a solid support having at least one surface comprising one or more ionic polymers of the invention.

Another aspect of the present invention provides a polymer membrane incorporating one or more ionic polymers of the invention.

Another aspect of the present invention provides use of the ionic polymers of the invention or a combination thereof, the solid support of the invention or the polymer membrane of the invention to produce fine chemicals from biomass.

Another aspect of the present invention provides a method for producing one or more fine chemicals selected from the group comprising lipids, sugars, furanic compounds, and/or humins from biomass, the method comprising the steps of:
a) providing biomass;
b) optionally determining lipids and/or sugars contents in the biomass;
c) optionally pretreating the biomass;
d) contacting the biomass with a catalyst to form a reaction mixture, wherein the catalyst is an ionic polymer of the invention or a combination of ionic polymers of the invention, a membrane incorporating ionic polymers of the invention and/or a solid-supported ionic polymers of the invention;
e) degrading the biomass in the reaction mixture to produce a liquid phase and a solid phase, wherein the liquid phase includes the one or more fine chemicals, and the solid phase includes residual biomass;
f) isolating at least a portion of the liquid phase from the solid phase; and
g) recovering the one or more fine chemicals from the isolated liquid phase.

Another aspect of the present invention provides a method for producing $C_5$ and $C_6$ sugars, furfural, 5-hydroxymethylfurfural (HMF) and derivatives of HMF from biomass, the method comprising the steps of:
a) providing biomass;
b) optionally determining sugars contents in the biomass;
c) optionally pretreating the biomass;
d) contacting the biomass with a catalyst to form a reaction mixture, wherein the catalyst is an ionic polymer of the invention or a combination of ionic polymers of the invention, a membrane incorporating ionic polymers of the invention and/or a solid-supported ionic polymers of the invention;

e) degrading the biomass in the reaction mixture to produce a first liquid phase and a first solid phase, wherein the first liquid phase includes $C_5$ oligomer sugars and/or $C_5$ monomer sugars and can further include furfural if the time of degrading step is extended, and the first solid phase includes residual material;

f) isolating at least a portion of the first liquid phase from the first solid phase;

g) recovering $C_5$ oligomer sugars and/or $C_5$ monomer sugars and/or furfural from the isolated first liquid phase;

h) contacting the first solid phase that includes residual material with the same catalyst as in step d) or with a different catalyst, to form a reaction mixture, wherein the catalyst is an ionic polymer of the invention or a combination of ionic polymers of the invention, a membrane incorporating ionic polymers of the invention and/or a solid-supported ionic polymers of the invention;

i) further degrading the first solid phase that includes residual material in the reaction mixture to produce a second liquid phase and a second solid phase, wherein the second liquid phase includes $C_6$ oligomer sugars and/or $C_6$ monomer sugars and can further include 5-hydroxymethylfurfural (HMF) and derivatives of HMF and/or humins if the time of degrading step is extended, and the second solid phase includes residual material;

j) isolating at least a portion of the second liquid phase from the second solid phase; and k) recovering $C_6$ oligomer sugars and/or $C_6$ monomer sugars and/or 5-hydroxymethylfurfural (HMF) and derivatives of HMF and/or humins from the isolated second liquid phase.

DETAILED DESCRIPTION OF THE INVENTION

Figure 1:
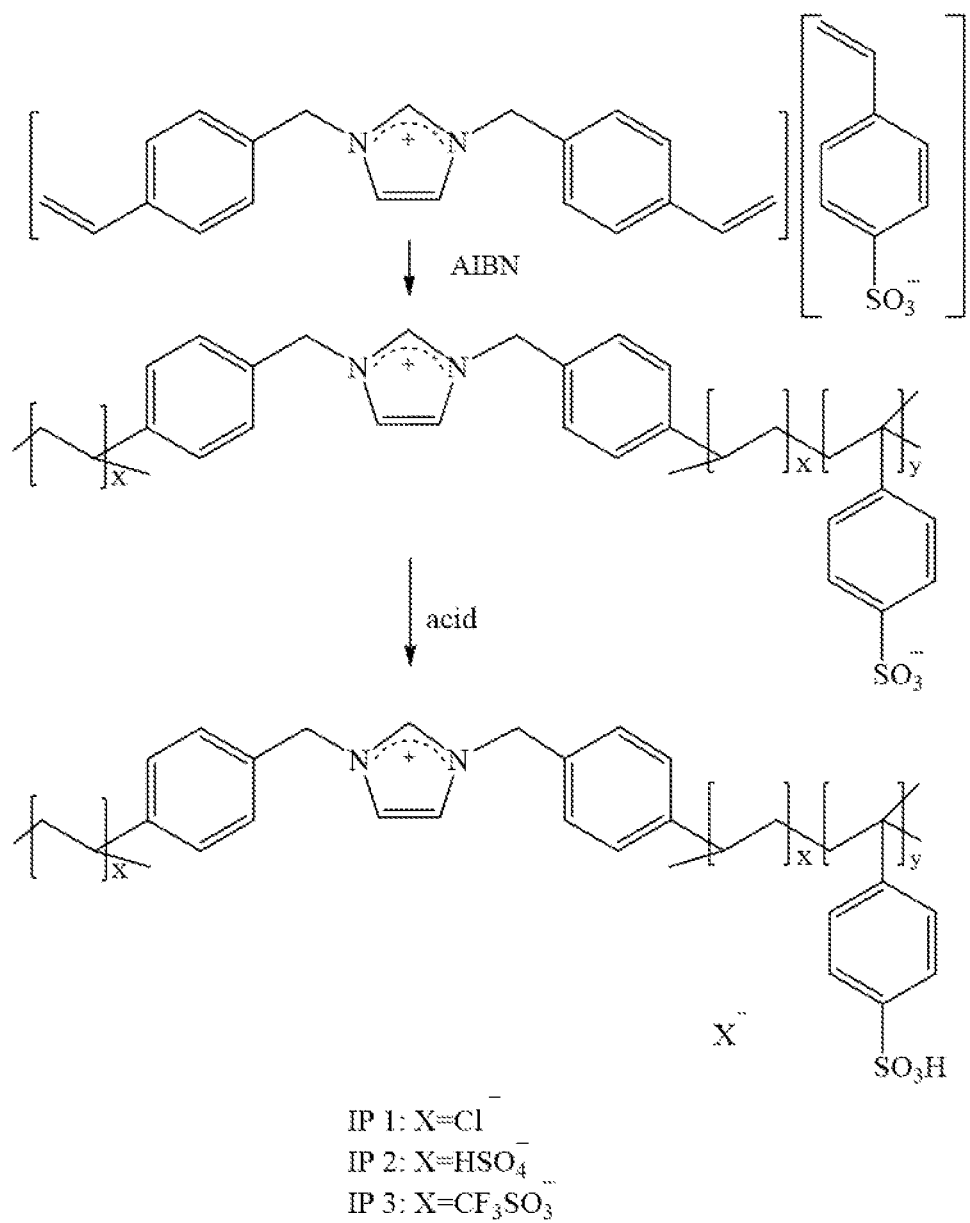
FIG. 1 shows generalized acidic polymer preparation scheme. For further reference: poly[1,3-bi(4-vinylbenzylimidazolium)-co-4-vinylbenzylsulfonium][chloride]-(IP 1), poly[1,3-bi(4-vinylbenzylimidazolium)-co-4-vinylbenzylsulfonium][hydrogen sulfate]-(IP 2), poly[1,3-bi(4-vinylbenzylimidazolium)-co-4-vinylbenzylsulfonium][triflate]-(IP 3).

All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" is generally used in the sense of include, that is to say permitting the presence of one or more features or components. Also as used in the specification and claims, the language "comprising" can include analogous embodiments described in terms of "consisting of" and/or "consisting essentially of".

As used in the specification and claims, the singular form "a", "an" and "the" include plural references unless the context clearly dictates otherwise.

As used in the specification and claims, the term "and/or" used in a phrase such as "A and/or B" herein is intended to include "A and B", "A or B", "A", and "B".

An "allyl" group is a substituent with the structural formula $H_2C=CH-CH_2R$, where R is the rest of the molecule.

An aspect of the invention provides ionic polymers consisting of anions and a polymeric backbone containing cations. Specifically, the invention provides an ionic polymer (IP) of formula (I) consisting of anions and a polymeric backbone containing cations

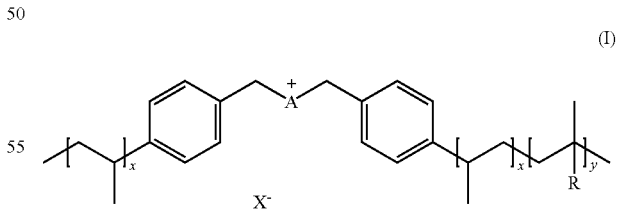

(I)

wherein

R is selected from substituted $C_1$-$C_{20}$ alkyl and substituted $C_5$-$C_{10}$ aryl, wherein substituents are selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)]; preferably R is substituted $C_6$ aryl and the substituents are selected from the group comprising H, —$SO_3H$.

A is a cation selected from the group comprising

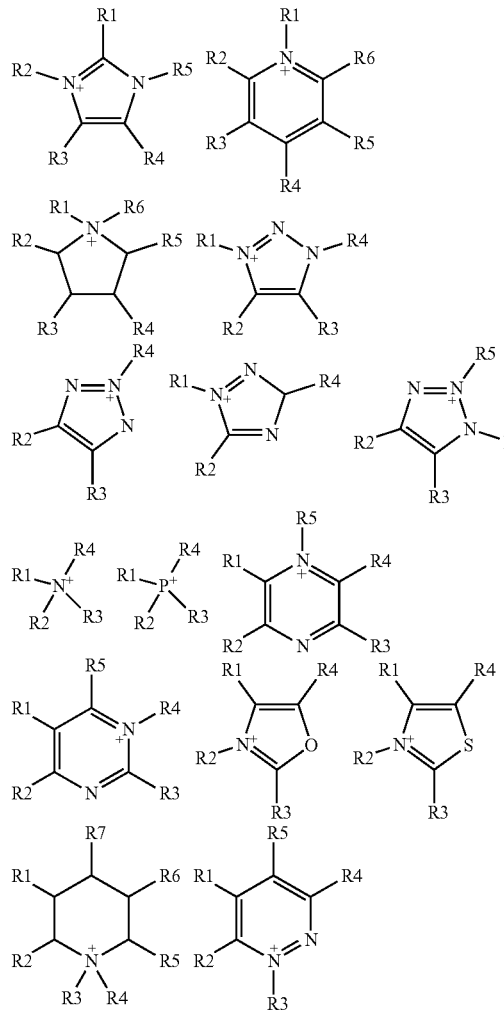

R1, R2, R3, R4, R5, R6 and R7 are each independently selected from the group comprising a bond, H, $C_1$-$C_6$ alkyl, allyl, $CH_3$—$(CH_2)n$—O—$(CH_2)m$-$CH_3$, $C_1$-$C_6$ alkoxy, $C_1$-$C_6$ alkoxyalkyl, benzyl, —$SO_3H$, provided that two of R1, R2, R3, R4, R5, R6 and R7 are each a bond to the polymeric backbone;

n and m are independently selected from 0, 1, 2, 3, 4, 5, 6;

x and y are integers each independently selected within the range 1 to 1000; preferably 1 to 500 or 1 to 200; more preferably 1 to 100 or 1 to 50;

X can be any suitable anion. In preferred embodiments, X is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate;

In some preferred embodiments, $C_1$-$C_6$ carboxylate are selected from the group comprising formate, acetate, propionate, butyrate, hexanoate, maleate, fumarate, oxalate, lactate, pyruvate.

In an embodiment, the invention provides the ionic polymer (IP) of formula (II)

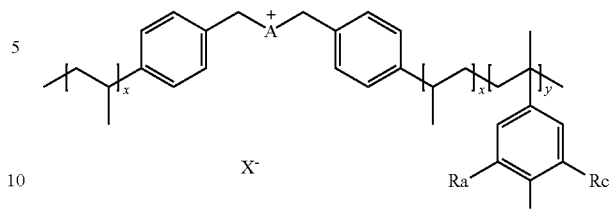

(II)

wherein
A is a cation selected from the group comprising

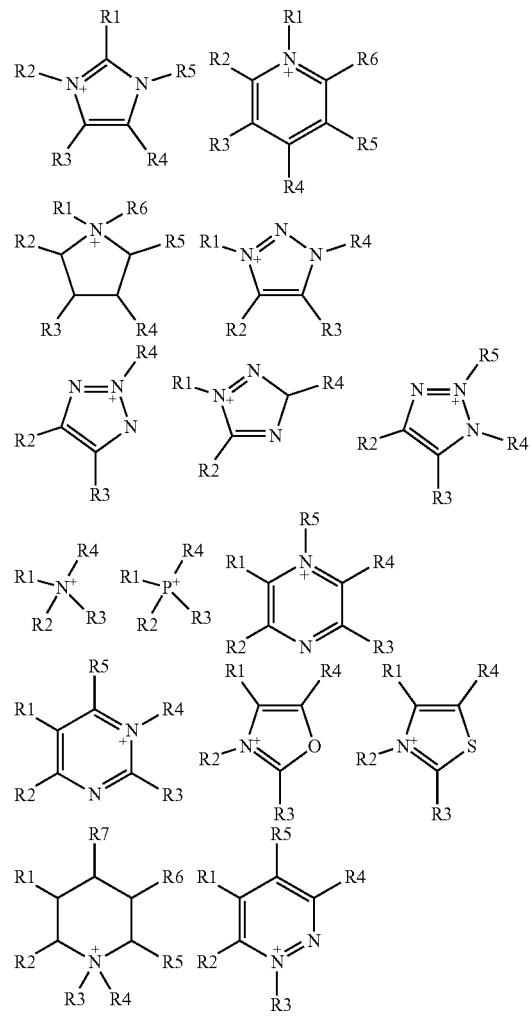

R1, R2, R3, R4, R5, R6 and R7 are each independently selected from the group comprising a bond, H, $C_1$-$C_6$ alkyl, allyl, $CH_3$—$(CH_2)n$—O—$(CH_2)m$-$CH_3$, $C_1$-$C_6$ alkoxy, $C_1$-$C_6$ alkoxyalkyl, benzyl, —$SO_3H$, provided that two of R1, R2, R3, R4, R5, R6 and R7 are each a bond to the polymeric backbone;

n and m are independently selected from 0, 1, 2, 3, 4, 5, 6;

x and y are integers each independently selected within the range 1 to 1000; preferably 1 to 500 or 1 to 200; more preferably 1 to 100 or 1 to 50;

X can be any suitable anion. In preferred embodiments, X is selected from the group comprising F$^-$, Cl$^-$, Br$^-$, I$^-$, ClO$_4^-$, BF$_4^-$, PF$_6^-$, AsF$_6^-$, SbF$_6^-$, NO$_2^-$, NO$_3^-$, HSO$_4^-$, SO$_4^{2-}$, PO$_4^{3-}$, HPO$_4^{2-}$, CF$_3$CO$_2^-$, CF$_3$CO$_3^-$, CO$_3^{2-}$, CF$_3$SO$_3^-$, C$_1$-C$_6$ carboxylate, CN$^-$, SCN$^-$, OCN$^-$, CNO$^-$, N$_3^-$, tosylate, mesylate, trifluoromethanesulfonate, trifluoroethane sulfonate, di-trifluoromethanesulfonyl amino, docusate, xylenesulfonate;

Ra, Rb, Rc are each independently selected from H, —SO$_3$H, —COOH, —[P(=O)(OH)$_2$], —[P(=O)(OH)], —O—SO$_3$H, —O—COOH, O[P(=O)(OH)$_2$], —O—[P(=O)(OH)]. Preferably Ra, Rb, Rc are selected from the group comprising H, —SO$_3$H.

In some preferred embodiments, C$_1$-C$_6$ carboxylate are selected from the group comprising formate, acetate, propionate, butyrate, hexanoate, maleate, fumarate, oxalate, lactate, pyruvate.

In another embodiment, the invention provides the ionic polymer (IP) of the following formula

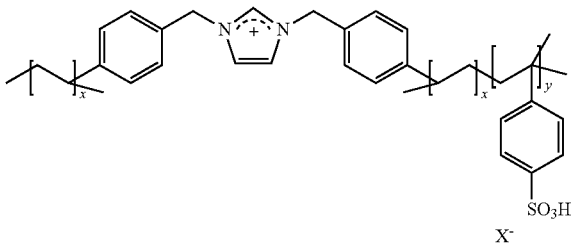

IP 1: X = Cl$^-$
IP 2: X = HSO$_4^-$
IP 3: X = CF$_3$SO$_3^-$

Ionic polymers (IPs) of the invention can be synthesized via several strategies, including but not limited to the direct polymerization of appropriate ionic species, the chemical modification of non-IPs, etc. (see for example FIG. 1). Polymerization may include different approaches, e.g. free radical polymerization, living/controlling radical polymerization, reversible addition-fragmentation transfer, ionic and coordination polymerization. The anionic structure can be designed according to preference before or after polymerization. The resulting ionic polymer (IP) combines the general properties of the ionic monomer and the enabling properties of a solid catalyst due to the presence of acidic groups. In an embodiment of the invention, a salt is prepared with a cation and an anion, wherein both the cation and the anion contain styrene groups that can be polymerized using AIBN. It is essentially a very simple method and the ionic polymer is purified by removal of the excess AIBN by washing and filtration. In a specific embodiment of the invention, a salt that is composed of the 1,3-di-styrene imidazolium cation and sulfonated styrene anion is prepared. This salt, a pure compound, is then polymerized using the radical initiator AIBN. The ionic polymer is purified by removal of the excess AIBN by washing and filtration. In the final step, the ionic polymer is protonated by addition of CF$_3$SO$_3$H.

The ionic polymers of the invention can be incorporated in membranes or attached to solid supports.

Another aspect of the invention provides membranes composed of ionic polymers of the invention. In some embodiments, the invention provides a polymer membrane comprising one or more ionic polymers of the invention. By adding appropriate copolymer (for example acrylic acid) to the salt used for preparation of ionic polymers of the invention and then polymerize the mixture it is possible to generate a polymer membrane. An approach for membrane formation is based on the template-free method via simple ionic complexations when an ionic monomer is copolymerized with appropriate organic acid/acid derivative (see Täuber K. et al, *Polym. Chem.*, 2015, 6, 4855-4858; Täuber K. et al, *ACS Macro Lett.*, 2015, 4(1), 39-42; Zhang S. et al, *Chem. Sci.*, 2015, 6, 3684-3691). As example, ionic monomer was dissolved in DMSO and stirred for 2 h at 60° C. The transparent solution was then poured onto a glass plate and the solvent was evaporated at 80° C. in an oven. The resulting non-porous dry polymer film was subsequently immersed into aqueous ammonia (0.2 wt %) overnight for pore formation and electrostatic complexation. The membrane was detached easily from the glass plate, washed several times with water and protonated afterwards in presence of triflic acid aquatic solution. The obtained product was washed with water.

Another aspect of the invention provides solid-supported ionic polymers. In some embodiments, the invention provides a solid support having at least one surface comprising one or more ionic polymers of the invention. Supported ionic polymers can be immobilized on different materials as a support: silicon or carbon (nanotube, wire) source, graphene or graphene oxide, zeolites, metal/metals alloys or metal/metal alloy oxides. As example, FeOx support has been oxidized in the oven in presence of oxygen at high temperature (500° C.) and its surface was modified with mixture of silanes dissolved in ethanol in presence of HCl afterwards. After drying at room temperature the support was uniformly impregnated with methanol solution of ionic polymer and AIBN. After drying at room temperature, the obtained material was placed in the oven at 95° C. for 2 h. By repeating the impregnation process the desire polymer loading might be achieved. Another example is stainless steel membrane comprising ionic polymers of the invention. A mixture containing ionic monomer (0.2-0.5, molar ratio), acrylic acid (0.1-0.6, molar ratio), and benzoin ethylether (1 wt %, as a photo-initiator) were dissolved in methanol to achieve a homogeneous solution, which was then dispersed by wettening onto stainless steel membrane and photo-crosslinked at room temperature by irradiation with UV light of 250 nm wavelength.

Ionic polymer attachment is also possible through surface grafting, which requires activation of the support by UV or O$_3$, O$_2$, H$_2$ or air plasmas. It involves the creation of reactive sites (radicals) on the polymer surface followed by the covalent linkage of a preformed polymer or, more commonly, by the polymerization of a monomer from those radical sites (see Alves P. et al, Colloids and Surfaces B: Biointerfaces, Volume 82, Issue 2, 1 Feb. 2011, 371-377; Barbey R. et al., *Chem. Rev.*, 2009, 109(11), 5437-5527). Another copolymer or polymerization initiator might also be used during the polymerisation process (as in case of membrane formation).

Another aspect of the invention provides use of ionic polymers of the invention or the combination thereof, membranes incorporating ionic polymers of the invention and/or solid-supported ionic polymers of the invention to produce fine chemicals (value added chemicals) from biomass. In preferred embodiments, the fine chemicals are lipids (for example fatty acids, mono-di- and tri-acylglycerides), sugars (for example monosaccharides, disaccharides, oligosaccharides), furanic compounds (for example furfural, 5-hydroxymethylfurfural (HMF) and HMF derivatives) and/or humins.

Another aspect of the invention provides a method that involves the use of the ionic polymers of the invention or the combination thereof, membranes incorporating ionic polymers of the invention and/or solid-supported ionic polymers of the invention for producing fine chemicals (value added chemicals) from biomass. In preferred embodiments, the fine chemicals are lipids (for example fatty acids, mono-di- and tri-acylglycerides), sugars (for example monosaccharides, disaccharides, oligosaccharides), furanic compounds (for example furfural, 5-hydroxymethylfurfural (HMF) and HMF derivatives) and/or humins.

In the context of the present invention, lipids are preferably mono-di- and tri-acylglycerides or fatty acids, such as hexanedecenoic acid, palmitic acid, octanedecenoic acid and stearic acid.

In the context of the present invention, sugars refer to monosaccharides, disaccharides, or oligosaccharides. Monosaccharides include glucose, fructose and galactose, mannose, xylose and other C6 and C5 sugars. Disaccharides including sucrose, maltose, lactose and other possible combinations of monocacharides. Oligosaccharides include longer chains of C6 and/or C5 sugars. In some embodiments, the sugars are one or more monosaccharides, one or more oligosaccharides, or a mixture thereof. In other embodiments, the sugars are two or more sugars that include at least one C5-C6 monosaccharide and at least one oligosaccharide. In yet other embodiments, the sugars are selected from glucose, galactose, fructose, xylose, and arabinose.

The sugars obtained by the methods of the present invention may be used as a food agent, for example, as a sweetening or flavouring agent, bulking agents or as substrates for fermentation and chemical conversion process. The sugars obtained by the methods of the present invention may be used for human and animal consumption or for non-human and non-animal consumption. In a preferred embodiment, the sugars obtained by the methods of the present invention are food grade sugars, suitable for human and animal consumption.

In the context of the present invention, furanic compounds are selected from the group consisting of furfural, 5-hydroxymethylfurfural (HMF) and derivatives of HMF likewise alkoxymethylfurfural, such as methoxymethylfurfural (MMF); and haloalkylfurfurals, such as 5-chloromethylfurfural. Also in the context of the present invention, furanic compounds can be obtained/derived from sugars that are obtained by methods of the present invention.

In the context of the present invention, humins can be obtained/derived from sugars that are obtained by methods of the present invention.

The term "biomass," as used herein, refers to living or dead biological material that can be used in one or more of the disclosed methods and processes of the invention. Biomass can comprise any cellulosic, chitinous, oleaginous or lignocellulosic material and includes materials comprising cellulose, and optionally further comprising hemicellulose, lignin, starch, oligosaccharides and/or monosaccharides, biopolymers, natural derivatives of biopolymers, their mixtures, and breakdown products (e.g., metabolites). Biomass can also comprise additional components, such as salts, proteins and/or lipids. Biomass can be derived from a single source, or biomass can comprise a mixture derived from more than one source. Some specific examples of biomass include, but are not limited to, bioenergy crops, agricultural residues, agricultural and food process by-products, municipal solid/liquid waste, industrial solid/liquid waste, sludge from paper manufacture, yard waste, wood and forestry waste. Additional examples of biomass include, but are not limited to, corn grain, corn cobs, crop residues such as corn husks, corn stover, grasses, wheat, wheat straw, hay, rice straw, switchgrass, waste paper, sugar cane bagasse, sorghum, soy, components obtained from milling of grains, trees (e.g., pine), branches, roots, leaves, wood chips, wood pulp, sawdust, shrubs and bushes, vegetables, fruits, flowers, animal manure, multi-component feed, and crustacean biomass (i.e., chitinous biomass). In a preferred embodiment, biomass is selected from the group comprising cellular biomass, food wastes/residues/side-streams, agricultural wastes, forestry wastes, timber wastes, processed wood, paper, pulp, algae, energy crops, fast-growing trees/plants. In another preferred embodiment, biomass is selected from the group consisting of cellulose, hemicelluloses, lignocelluloses and mixtures thereof.

According to some embodiments of the invention, it is possible to use a mixture of the ionic polymers of the invention in the uses of the inventions and in the methods of the invention. Ionic polymers mixture can be obtained either by physical mixing of each ionic polymer of the invention or by protonation reaction (last step in preparation) in a mixture of appropriate acids (for example HCl and $H_2SO_4$).

Essentially, the biomass is heated in the presence of one or more ionic polymers of the invention, membranes incorporating ionic polymers of the invention and/or solid-supported ionic polymers of the invention in water or organic solvent to obtain fine chemicals, such as lipids, sugars, furanic compounds, and/or humins depending on the type of biomass used, pretreatment steps of the biomass and the reaction conditions (time, temperatures, solvents and other reagents).

Another aspect of the invention provides a method for producing one or more fine chemicals selected from the group comprising lipids, sugars, furanic compounds, and/or humins from biomass, the method comprising the steps of:
  a) providing biomass;
  b) optionally determining lipids and/or sugars contents in the biomass;
  c) optionally pretreating the biomass;
  d) contacting the biomass with a catalyst to form a reaction mixture, wherein the catalyst is an ionic polymer of the invention or a combination of ionic polymers of the invention, a membrane incorporating ionic polymers of the invention and/or a solid-supported ionic polymers of the invention;
  e) degrading the biomass in the reaction mixture to produce a liquid phase and a solid phase, wherein the liquid phase includes the one or more fine chemicals, and the solid phase includes residual biomass;
  f) isolating at least a portion of the liquid phase from the solid phase; and
  g) recovering the one or more fine chemicals from the isolated liquid phase.

In one embodiment, the step d) contacting the biomass with a catalyst to form a reaction mixture consists in adding an appropriate water or organic solvent and an effective amount of the catalyst to the biomass to form a reaction mixture, wherein the catalyst is an ionic polymer of the invention or a combination of ionic polymers of the invention, a membrane incorporating ionic polymers of the invention and/or a solid-supported ionic polymers of the invention; and degrading step e) consists in heating the reaction mixture of step d) during appropriate time and subsequently cooling to room temperature (typically 20-25° C.).

An embodiment of the invention provides a method for producing one or more fine chemicals selected from the group comprising lipids, sugars, furanic compounds, and/or humins from biomass, the method comprising the steps of:

a) providing biomass
b) optionally determining lipids and/or sugars contents in the biomass;
c) optionally pretreating biomass;
d) adding an appropriate water or organic solvent and an effective amount of a catalyst to the biomass to form a reaction mixture, wherein the catalyst is an ionic polymer of the invention or a combination of ionic polymers of the invention, a membrane incorporating ionic polymers of the invention and/or a solid-supported ionic polymers of the invention;
e) heating the mixture of step d) during appropriate time;
f) cooling to room temperature;
g) recovering the one or more fine chemicals.

In some embodiments of the method of the present invention, the organic solvent is selected from the group comprising alcohol (such as methanol, ethanol, butanol, ethylene glycol, etc.), ether (such as dimethoxyethane, diglyme, butyl methyl ether, etc.), ketone (such as methyl isobutyl ketone, N-methyl-2-pyrrolidone, etc.), DMSO, DME, DMF, THF, ionic liquids. In some embodiments, ionic liquids used as organic solvent in the methods of the invention comprise cation and anion moieties and are referred as green organic solvents as they are non-volatile and therefore can be easily contained. Cations present in ionic liquids of the invention are choline, imidazolium, pyrrolidinium, pyridinium, ammonium and phosphonium based cations and/or selected from the group comprising

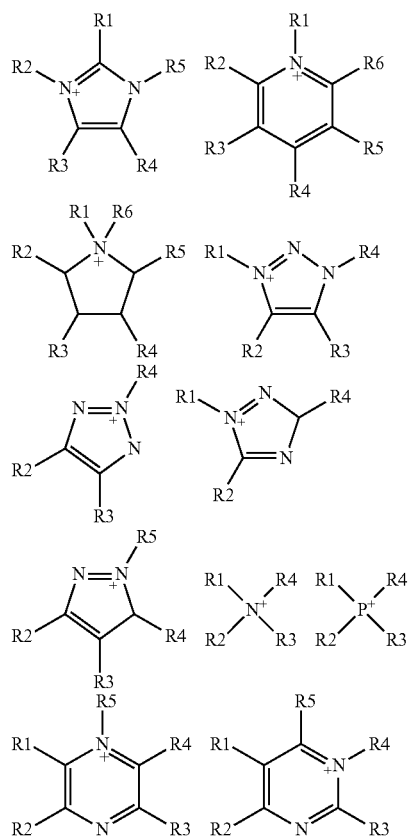

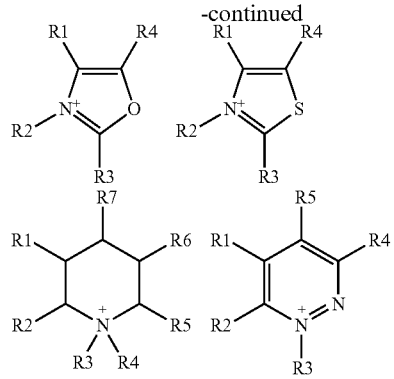

wherein R1, R2, R3, R4, R5, R6 and R7 are each independently selected from the group comprising a bond, H, $C_1$-$C_6$ alkyl, allyl, $CH_3$—$(CH_2)n$-O—$(CH_2)m$-$CH_3$, $C_1$-$C_6$ alkoxy, $C_1$-$C_6$ alkoxyalkyl, benzyl, —$SO_3H$.

Anions present in the ionic liquids of the invention can be any suitable anion. In preferred embodiments, anion is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate.

In some embodiments of the methods of the present invention, recovering the one or more fine chemicals, such as lipids, sugars, furanic compounds, and/or humins can be done by any technic known in the art, such as filtration, centrifugation or gravity settling.

In the context of the present invention, decomposing or degrading biomass encompasses also transforming and hydrolysing biomass, extracting from biomass compounds or fine chemicals of interest, such as lipids, sugars, furanic compounds, and/or humins, or any other activity that allows decomposition, degradation, transformation of biomass into compounds or fine chemicals of interest.

Some embodiments of the invention provide methods of producing one or more sugars from various biomass using ionic polymers of the invention or a combination thereof, membranes incorporating ionic polymers of the invention and/or solid-supported ionic polymers of the invention to decompose or degrade biomass.

In some embodiments, the methods described herein using the ionic polymers of the invention or a combination thereof, membranes incorporating ionic polymers of the invention and/or solid-supported ionic polymers of the invention can hydrolyse the cellulose and/or hemicellulose into one or more sugars, including monosaccharides, disaccharides, and/or oligosaccharides.

An embodiment of the invention provides a method for producing one or more sugars from biomass, the method comprising the steps of:

a) providing biomass;
b) optionally determining sugars contents in the biomass;
c) optionally pretreating the biomass;
d) contacting the biomass with a catalyst to form a reaction mixture, wherein the catalyst is an ionic polymer of the invention or a combination of ionic polymers of the invention, a membrane incorporating ionic polymers of the invention and/or a solid-supported ionic polymers of the invention;

e) degrading the biomass in the reaction mixture to produce a liquid phase and a solid phase, wherein the liquid phase includes one or more sugars, and the solid phase includes residual biomass;

f) isolating at least a portion of the liquid phase from the solid phase; and g) recovering the one or more sugars from the isolated liquid phase.

In some embodiments, biomass can be subjected to a multi-step degradation, such as hydrolysis process. For example, in some embodiments, biomass containing C5 and C6 sugars can be first contacted with the ionic polymers of the invention or the combination thereof, membranes incorporating ionic polymers of the invention and/or solid-supported ionic polymers of the invention to recover only C5 oligomer sugars or C5 monomer sugars, that can further provide furfural if the reaction time is extended and then the residual material with the addition of appropriate solvent is further processed in a second degradation step (for example hydrolysis step) to recover C6 oligomer sugars and/or C6 monomer sugars, that can further provide 5-hydroxymethylfurfural (HMF) and derivatives thereof if the reaction time is extended. Temperature and reaction time of each step is individually set for optimizing extraction. Typically a multi-step process requires extended reaction time comparing to the one-step process. If the ionic polymer of the invention or the combination of ionic polymers of the invention is unsupported, then it stays in the first solid phase that includes residual material. If the ionic polymer of the invention or the combination of ionic polymers of the invention is supported it stays on the support. In any case, in this multi-step process it is not necessary to add or reintroduce again ionic polymers of the invention or the combination thereof. Thus another embodiment of the invention provides a method for producing C5 and C6 sugars, furfural, 5-hydroxymethylfurfural (HMF) and derivatives of HMF from biomass, the method comprising the steps of:

a) providing biomass;

b) optionally determining sugars contents in the biomass;

c) optionally pretreating the biomass;

d) contacting the biomass with a catalyst to form a reaction mixture, wherein the catalyst is an ionic polymer of the invention or a combination of ionic polymers of the invention, a membrane incorporating ionic polymers of the invention and/or a solid-supported ionic polymers of the invention;

e) degrading the biomass in the reaction mixture to produce a first liquid phase and a first solid phase, wherein the first liquid phase includes C5 oligomer sugars and/or C5 monomer sugars and can further include furfural if the time of degrading step is extended, and the first solid phase includes residual material;

f) isolating at least a portion of the first liquid phase from the first solid phase;

g) recovering C5 oligomer sugars and/or C5 monomer sugars and/or furfural from the isolated first liquid phase;

h) contacting the first solid phase that includes residual material with the same catalyst as in step d) or with a different catalyst, to form a reaction mixture, wherein the catalyst is an ionic polymer of the invention or a combination of ionic polymers of the invention, a membrane incorporating ionic polymers of the invention and/or a solid-supported ionic polymers of the invention;

i) further degrading the first solid phase that includes residual material in the reaction mixture to produce a second liquid phase and a second solid phase, wherein the second liquid phase includes C6 oligomer sugars and/or C6 monomer sugars and can further include 5-hydroxymethylfurfural (HMF) and derivatives of HMF and/or humins if the time of degrading step is extended, and the second solid phase includes residual material;

j) isolating at least a portion of the second liquid phase from the second solid phase; and k) recovering C6 oligomer sugars and/or C6 monomer sugars and/or 5-hydroxymethylfurfural (HMF) and derivatives of HMF and/or humins from the isolated second liquid phase.

In some embodiments of the multi-step degradation method of the invention, it is understood that the catalyst in step h) can be already present in the process (in the first solid phase, in the membrane and/or supported) and therefore it is the same as in step d) of the method or it can be different, i.e. subsequently added.

In another embodiment of the invention, decomposition reactions of the biomass containing cellulose and hemicellulose can be allowed to continue towards the formation of other value-added chemicals such as 5-hydroxymethylfurfural (HMF) and its derivatives, furfural and humins. In this decomposition reaction, the reaction time is typically longer than the reaction time necessary for obtaining C5/C6 oligomer sugars and/or C5/C6 monomer sugars. HMF is a versatile platform chemical and a precursor to other platform and value added chemicals. Thus an embodiment of the invention provides a method for producing 5-hydroxymethylfurfural (HMF) or derivatives thereof, furfural and/or humins from biomass, the method comprising the steps of:

a) providing biomass;

b) optionally determining sugars contents in the biomass;

c) optionally pretreating the biomass;

d) contacting the biomass with a catalyst to form a reaction mixture, wherein the catalyst is an ionic polymer of the invention or a combination of ionic polymers of the invention, a membrane incorporating ionic polymers of the invention and/or a solid-supported ionic polymer of the invention;

e) degrading the biomass in the reaction mixture to produce a liquid phase and a solid phase, wherein the liquid phase includes 5-hydroxymethylfurfural or derivatives thereof, furfural or humins, and the solid phase includes residual biomass;

f) isolating at least a portion of the liquid phase from the solid phase; and g) recovering 5-hydroxymethylfurfural or derivatives thereof, furfural or humins from the isolated liquid phase.

Optionally, prior to any use, sugars and/or lipids contents are determined in the biomass based on the standard methods. Lipids can be determined/extracted using Folch method (Folch J, Lees M, Stanley, G H S, 1957, 226, 497-509) involving a mixture of methanol, chloroform and water (2:1:0.8, v/v/v), and phase separation afterwards. Determination of sugars is performed according, for example, NREL protocol for "Determination of Structural Carbohydrates and Lignin in Biomass". For example, 1 ml of 72% sulfuric acid was added to 100 mg of biomass. The slurry was stirred for 1 h at 30° C., followed by addition of 28 ml of deionized water. Mixture was autoclaved at 120 C for 1 h, cooled to room temperature and was used for sugar analysis by HPLC and acid-soluble lignin determination using UV-spectrophotometry at 205 nm wavelength. The same hydrolysate was used for proteins analysis according the Bradford protein assay. The residue from acid hydrolysis was washed with 100 mL of water and then dried at 105° C. to determine Klason lignin.

The optional pretreatment of the biomass, used in the methods described herein, uses one or more methods selected from the group consisting of washing, solvent-extraction, solvent-swelling, comminution, milling, steam pretreatment, explosive steam pretreatment, dilute acid pretreatment, hot water pretreatment, alkaline pretreatment, lime pretreatment, wet oxidation, wet explosion, ammonia fiber explosion, organosolvent pretreatment, biological pretreatment, ammonia percolation, ultrasound, electroporation, microwave, supercritical $CO_2$, supercritical $H_2O$, ozone, and gamma irradiation. The optional pretreatment of the biomass includes for example the milling of the biomass. To overcome the obstacle of the reaction rate being limited by the surface reaction and mass transfer, a pretreatment processes of the biomass via ball milling, which leads to a reduction in crystallinity and an increase in the specific surface area of cellulosic material, is highly recommended. Depending on performed mechanical ball milling of biomass there is a decrease in structural particle size, reduction of the degree of polymerization of cellulose, and an increase in the amorphous content of cellulose.

The effective amount of the ionic polymers of the invention or a combination thereof used in the methods described herein can depend on several factors including, for example, the type of biomass, the amount of the biomass, the content of the sugars and/or lipids in the biomass, the type and number of pretreatment(s) applied to the biomass, and the reaction conditions (such as temperature and time). An effective amount of the ionic polymer of the invention refers to an amount sufficient to degrade biomass to, for instance, attain one or more desired sugars, lipids or other fine chemicals and value-added chemicals (such as 5-hydroxymethylfurfural (HMF) or its derivatives, furfural and humins). In some embodiments, the effective amount of the ionic polymer of the invention is usually 0.05:1 w/w to 10:1 w/w, 0.5:1 w/w to 10:1 w/w, 1:1 w/w to 1:5 w/w, preferably 0.1:1 w/w to 1:5 w/w compared to sugars content in the biomass.

The ratio biomass to water used in the methods described herein can depend on several factors, including for example the type of biomass and the amount of biomass. In some embodiments, the ratio biomass to water or organic solvent (such as alcohol, ether, ketone, DMSO, DME, DMF) used in the methods described herein is ranging from 1:100 w/v to 1:1 w/v, preferably 1:50 w/v to 1:10 w/v.

The preferred temperature profile for the heating used in the methods described herein depends on the biomass starting material being used and also the intended monomer and oligomer mixture being produced. The heating temperature should preferably be held at a maximum of 250° C., in some embodiments at a maximum of 200° C. In some embodiments, the heating temperature is between 100° C. and 250° C., or between 100° C. and 200° C. preferably between 120° C. to 220° C. or between 120° C. to 220° C. Preferably, for small-scale applications, the heating is done in a high-pressure autoclave reactor, which after sealing, is heated for appropriate reaction time and temperature.

In some embodiments, the appropriate reaction time in the methods described herein is for example between 10 minutes and 10 hours, preferably between 0.5 hour and 5 hours or between 1 hour and 3 hours, depending on the type and amount of biomass.

In some embodiments, the methods for producing one or more, sugars, furanic compounds and/or humins from biomass using the ionic polymers of the invention or a combination thereof, a membrane incorporating ionic polymers of the invention and/or a solid-supported ionic polymers of the invention, further include recovering the sugars, the furanic compounds and/or humins that are produced from the hydrolysis of biomass. The sugars and the furanic compounds, which are typically soluble, can be separated from the insoluble residual biomass using technology well known in the art such as, for example, centrifugation, filtration, and gravity settling.

Recovering of the sugars, the furanic compounds and/or humins can be performed in the hydrolysis reactor or in a separator vessel. In an exemplary embodiment, the method for producing one or more sugars, furanic compounds and/or humins from biomass is performed in a system with a hydrolysis reactor and a separator vessel. Reactor effluent containing the monosaccharides, disaccharides, oligosaccharides, furanic compounds and/or humins is transferred into a separator vessel and is washed with a solvent (for example water), by adding the solvent into the separator vessel and then separating the solvent in a continuous centrifuge. Alternatively, in another exemplary embodiment, a reactor effluent containing residual solids (for example residual biomass) is removed from the reactor vessel and washed, for example, by conveying the solids on a porous base (for example a mesh belt) through a solvent (for example water) wash stream. Following contact of the stream with the reacted solids, a liquid phase containing the monosaccharides, disaccharides, oligosaccharides, furanic compounds and/or humins is generated. Optionally, residual solids can be separated by a cyclone. Suitable types of cyclones used for the separation can include, for example, tangential cyclones, spark and rotary separators, and axial and multi-cyclone units.

In another embodiment, recovering of the sugars, the furanic compounds and/or humins is performed by batch or continuous differential sedimentation. Reactor effluent is transferred to a separation vessel, optionally combined with water and/or enzymes for further treatment of the effluent. Over a period of time, solid biomaterials (for example residual treated biomass), the catalyst (for example the ionic polymer of the invention), and the sugar-containing aqueous material, the furanic-containing aqueous material and/or humins-containing aqueous material can be separated by differential sedimentation into a plurality of phases (or layers). Generally, the catalyst layer can sediment to the bottom, and depending on the density of the residual biomass, the biomass phase can be on top of, or below, the aqueous phase. When the phase separation is performed in a batch mode, the phases are sequentially removed, either from the top of the vessel or an outlet at the bottom of the vessel. When the phase separation is performed in a continuous mode, the separation vessel contains one or more than one outlet means (for example two, three, four, or more than four), generally located at different vertical planes on a lateral wall of the separation vessel, such that one, two, or three phases are removed from the vessel. The removed phases are transferred to subsequent vessels or other storage means. By these processes, one of skill in the art would be able to capture (1) the catalyst layer and the aqueous layer or biomass layer separately, or (2) the catalyst, aqueous, and biomass layers separately, allowing efficient catalyst recycling, retreatment of biomass, and separation of sugars. Moreover, controlling rate of phase removal and other parameters allows for increased efficiency of catalyst recovery. Subsequent to removal of each of the separated phases, the catalyst and/or biomass can be separately washed by the aqueous layer to remove adhered sugars, furanic compounds and/or humins molecules.

In some embodiments, the sugars, the furanic compounds and/or humins isolated from the vessel can be subjected to further processing steps (for example as in drying, fermentation) to produce bio fuels and other bio-products.

The residual biomass isolated from the vessels can be useful as a combustion fuel, as fertilizer or as a feed source of non-human animals such as livestock or to a subsequent step for additional post-processing.

Another aspect of the invention provides a method that involves the use of the ionic polymers of the invention or a combination thereof, a membrane incorporating ionic polymers of the invention and/or a solid-supported ionic polymers of the invention for selectively converting polysaccharide polymers with a high degree of polymerization (DP) into mono- and oligosaccharides with a specific and/or lower degree of polymerization. For example, under optimized conditions it is possible to isolate only glucose/fructose or sugar oligomers with variable degree of polymerization (DP 2 DP 12).

Another aspect of the invention provides a method that involves the use of the ionic polymers of the invention or a combination thereof, a membrane incorporating ionic polymers of the invention and/or a solid-supported ionic polymers of the invention for extraction of lipids, such as fatty lipids, from biomass, wherein additional catalysts and/or additional gases ($CO_2$, $H_2$ etc.) are also used. For example, continuous extraction of the product or products may be employed, e.g. using an appropriate solvent or gas. As examples, supercritical $CO_2$ can be used in combination with the ionic polymer of the invention to extract lipids, leaving the remaining material to undergo transformation. If a catalyst such as Rh, Pt, Pd, their complex, salt or metal oxide, etc. is introduced to the reaction system in presence of $H_2$, the released sugars can be converted into alkanes.

The ionic polymers of the invention or a combination thereof, a membrane incorporating ionic polymers of the invention and/or a solid-supported ionic polymers of the invention can be used for extraction of lipids from biomass according to the methods known in the art (see Young, G. et al., Separation and Purification Technology 72, 118-121 (2010); Choi, S.-A. et al., Algal Research, 3, 44-48 (2014); Kim, Y.-H. et al., Bioresource Technology 109, 312-315 (2012); Sahena, F. et al., A review. Journal of Food Engineering 95, 240-253 (2009)).

The methods of the present invention can be used in diverse chemical, biotechnological and other industrial and non-industrial applications for transforming biomass to fine chemicals, simple constituents and subsequent derivatives and commodities.

The ionic polymers of the invention or a combination thereof and the methods of the invention have several advantages compared to the polymeric compound and methods of the prior art. For example, no ionic polymer leaching was observed. This allows the ionic polymers of the invention to be used for the biomass treatment and the recovered sugars to be considered as a food grade product. Further, the ionic polymer of the invention operates in water; there is no need for ionic liquid solvents and in some cases any other organic solvent. Since other polymeric compounds of the prior art operate in ionic liquids (ILs), separation of products is more complicated. Using the ionic polymers and the methods of the invention, the products are in water and can be easily separated by filtration. Also, the reaction is performed in water and altering the reaction conditions result in product variations with different degree of polymerization. Generally, reaction is taking place within a short reaction time. The method of the invention operates at moderate temperatures, typically less than 150° C., whereas the prior art methods needs temperatures of more than 150° C. In addition, the ionic polymers and the methods of the invention provide fewer by-products, which allows easier recovery of the desired products.

An important advantage of the ionic polymers of the invention or a combination thereof, membranes incorporating ionic polymers of the invention and/or solid-supported ionic polymers of the invention and use thereof for biomass hydrolysis, decomposition or degradation is their use in one-pot systems for decomposition and selective extracting the aforementioned useful fine chemicals (value added chemicals) from the biomass.

Further Instances of the Present Invention

1. An ionic polymer (IP) of formula (I) consisting of anions and a polymeric backbone containing cations

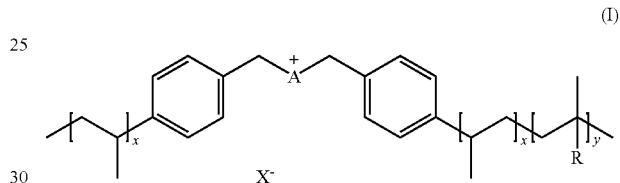

wherein
R is selected from substituted $C_1$-$C_{20}$ alkyl and substituted $C_5$-$C_{10}$ aryl, wherein substituents are selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)];
A is a cation selected from the group comprising

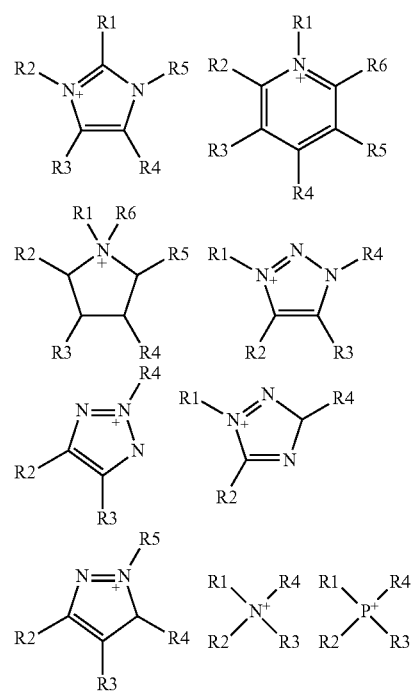

-continued

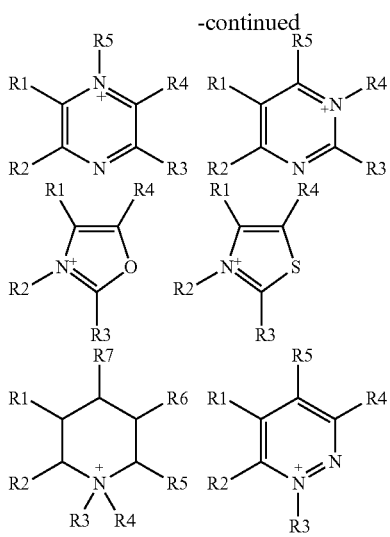

R1, R2, R3, R4, R5, R6 and R7 are each independently selected from the group comprising a bond, H, $C_1$-$C_6$ alkyl, allyl, $CH_3$—$(CH_2)n$-$O$—$(CH_2)m$-$CH_3$, $C_1$-$C_6$ alkoxy, $C_1$-$C_6$ alkoxyalkyl, benzyl, —$SO_3H$, provided that two of R1, R2, R3, R4, R5, R6 and R7 are each a bond to the polymeric backbone;

n and m are independently selected from 0, 1, 2, 3, 4, 5, 6;

x and y are integers each independently selected within the range 1 to 1000;

X is selected from the group comprising $F^-$, $Cl^-$, $Br^-$, $I^-$, $ClO_4^-$, $BF_4^-$, $PF_6^-$, $AsF_6^-$, $SbF_6^-$, $NO_2^-$, $NO_3^-$, $HSO_4^-$, $SO_4^{2-}$, $PO_4^{3-}$, $HPO_4^{2-}$, $CF_3CO_2^-$, $CF_3CO_3^-$, $CO_3^{2-}$, $CF_3SO_3^-$, $C_1$-$C_6$ carboxylate, $CN^-$, $SCN^-$, $OCN^-$, $CNO^-$, $N_3^-$, tosylate, mesylate, trifluoromethanesulfonate, trifluoroethane sulfonate, di-trifluoromethanesulfonyl amino, docusate, xylenesulfonate;

2. The ionic polymer of instance 1, wherein R is substituted $C_1$-$C_{20}$ alkyl, preferably $C_2$-$C_{10}$ alkyl, wherein substituents are selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)];

3. The ionic polymer of instance 1, wherein R is substituted $C_5$-$C_{10}$ aryl, preferably $C_5$-$C_6$ aryl, wherein substituents are selected from the group comprising H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)];

4. The ionic polymer of instance 1 or 3, wherein R is substituted $C_6$ aryl and the substituents are selected from the group comprising H, —$SO_3H$.

5. The ionic polymer of instance 1 represented by formula (II)

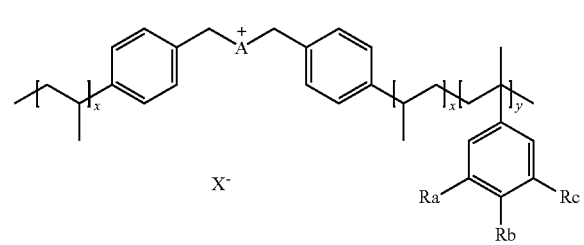

(II)

wherein
Ra, Rb, Rc are each independently selected from H, —$SO_3H$, —COOH, —[P(=O)(OH)$_2$], —[P(=O)(OH)], —O—$SO_3H$, —O—COOH, —O—[P(=O)(OH)$_2$], —O—[P(=O)(OH)].

6. The ionic polymer of instance 1 represented by

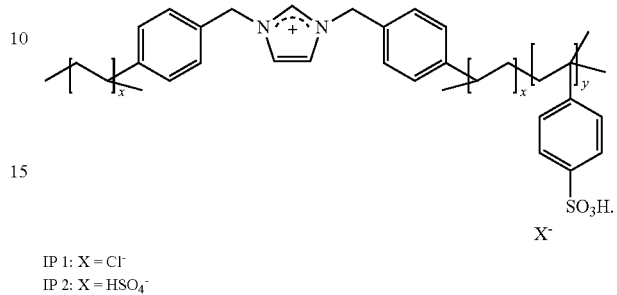

IP 1: X = $Cl^-$
IP 2: X = $HSO_4^-$
IP 3: X = $CF_3SO_3^-$

7. A solid support having at least one surface comprising one or more ionic polymers of any one of instances 1-6.

8. A polymer membrane incorporating one or more ionic polymers of any one of instances 1-6.

9. Use of ionic polymers of any one of instances 1-6 or a combination thereof, the solid support of instance 7 or the polymer membrane of instance 8 to produce fine chemicals from biomass.

10. The use of instance 7, wherein the fine chemicals are selected from the group comprising lipids, sugars, furanic compounds and humins.

11. A method for producing one or more fine chemicals selected from the group comprising lipids, sugars, furanic compounds, and/or humins from biomass, the method comprising the steps of:
  a) providing biomass;
  b) optionally determining lipids and/or sugars contents in the biomass;
  c) optionally pretreating the biomass;
  d) contacting the biomass with a catalyst to form a reaction mixture, wherein the catalyst is an ionic polymer of any one of instances 1-6 or a combination of ionic polymers of any one of instances 1-6, a membrane incorporating ionic polymers of any one of instances 1-6 and/or a solid-supported ionic polymers of instance 7;
  e) degrading the biomass in the reaction mixture to produce a liquid phase and a solid phase, wherein the liquid phase includes the one or more fine chemicals, and the solid phase includes residual biomass;
  f) isolating at least a portion of the liquid phase from the solid phase; and
  g) recovering the one or more fine chemicals from the isolated liquid phase.

12. The method of instance 11, wherein the step d) consists in adding an appropriate water or organic solvent and an effective amount of the catalyst to the biomass to form a reaction mixture, and degrading step e) consists in heating the reaction mixture of step d) during appropriate time and subsequently cooling to room temperature.

13. The method of instance 11 or 12, wherein the fine chemical is sugar.

14. A method for producing C5 and C6 sugars, furfural, 5-hydroxymethylfurfural (HMF) and derivatives of HMF from biomass, the method comprising the steps of:

a) providing biomass;
b) optionally determining sugars contents in the biomass;
c) optionally pretreating the biomass;
d) contacting the biomass with a catalyst to form a reaction mixture, wherein the catalyst is an ionic polymer of any one of instances 1-6 or a combination of ionic polymers of any one of instances 1-6, a membrane incorporating ionic polymers of any one of instances 1-6 and/or a solid-supported ionic polymers of instance 7;
e) degrading the biomass in the reaction mixture to produce a first liquid phase and a first solid phase, wherein the first liquid phase includes C5 oligomer sugars and/or C5 monomer sugars and can further include furfural if the time of degrading step is extended, and the first solid phase includes residual material;
f) isolating at least a portion of the first liquid phase from the first solid phase;
g) recovering C5 oligomer sugars and/or C5 monomer sugars and/or furfural from the isolated first liquid phase;
h) contacting the first solid phase that includes residual material with the same catalyst as in step d) or with a different catalyst, to form a reaction mixture, wherein the catalyst is an ionic polymer of any one of instances 1-6 or a combination of ionic polymers of any one of instances 1-6, a membrane incorporating ionic polymers of any one of instances 1-6 and/or a solid-supported ionic polymers of instance 7;
i) further degrading the first solid phase that includes residual material in the reaction mixture to produce a second liquid phase and a second solid phase, wherein the second liquid phase includes C6 oligomer sugars and/or C6 monomer sugars and can further include 5-hydroxymethylfurfural (HMF) and derivatives of HMF and/or humins if the time of degrading step is extended, and the second solid phase includes residual material;
j) isolating at least a portion of the second liquid phase from the second solid phase; and
k) recovering C6 oligomer sugars and/or C6 monomer sugars and/or 5-hydroxymethylfurfural (HMF) and derivatives of HMF and/or humins from the isolated second liquid phase.

15. The method of instance 14, wherein the step d) consists in adding an appropriate water or organic solvent and an effective amount of the catalyst to the biomass to form a reaction mixture, and degrading steps e) and i) consist in heating the reaction mixture during appropriate time and subsequently cooling to room temperature.

16. The method of instance 14 or 15, wherein time of degrading step is extended by at least for 10 minutes, by at least for 30 minutes, by at least for 1 hour, by at least for 2 hours, by at least for 3 hours, by at least for 5 hours, by at least for 7 hours, or by at least for 10 hours.

17. The method of instances 12, 13, 15 or 16, wherein the organic solvent is selected from the group comprising alcohol, ether, ketone, DMSO, DME, DMF, THF, ionic liquids.

18. The method of instances 12, 13, 15 or 16, wherein the organic solvent is selected from the group comprising alcohol, ether, ketone, DMSO, DME, DMF, THF.

19. The method of instances 12, 13, 15, 16 or 17, wherein the appropriate time is between 10 minutes and 10 hours, preferably between 0.5 hour and 5 hours or between 1 hour and 3 hours.

20. The method of any one of instances 11 to 19, wherein the membrane incorporating ionic polymers of any one of instances 1-6 is the membrane of instance 8.

21. The method of any one of instances 11 to 20, wherein recovering the one or more fine chemicals can be done by filtration, centrifugation or gravity settling.

22. The method of any one of instances 11 to 21, wherein the optional pretreatment of the biomass uses one or more pretreatment methods selected from the group consisting of washing, solvent-extraction, solvent-swelling, comminution, milling, steam pretreatment, explosive steam pretreatment, dilute acid pretreatment, hot water pretreatment, alkaline pretreatment, lime pretreatment, wet oxidation, wet explosion, ammonia fiber explosion, organosolvent pretreatment, biological pretreatment, ammonia percolation, ultrasound, electroporation, microwave, supercritical $CO_2$, supercritical $H_2O$, ozone, and gamma irradiation.

23. The method of any one of instances 12, 13, 15-22, wherein the heating temperature is held at a maximum of 250° C.

24. The method of any one instances 11 to 23, wherein the biomass is selected from the group comprising cellulosic, chitinous, oleaginous or lignocellulosic material.

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended claims, and all changes which come within the meaning and range of equivalency are intended to be embraced therein.

The foregoing description will be more fully understood with reference to the following Examples. Such Examples, are, however, exemplary of methods of practising the present invention and are not intended to limit the application and the scope of the invention.

EXAMPLES

Preparation of Ionic Polymers

Figure 3:
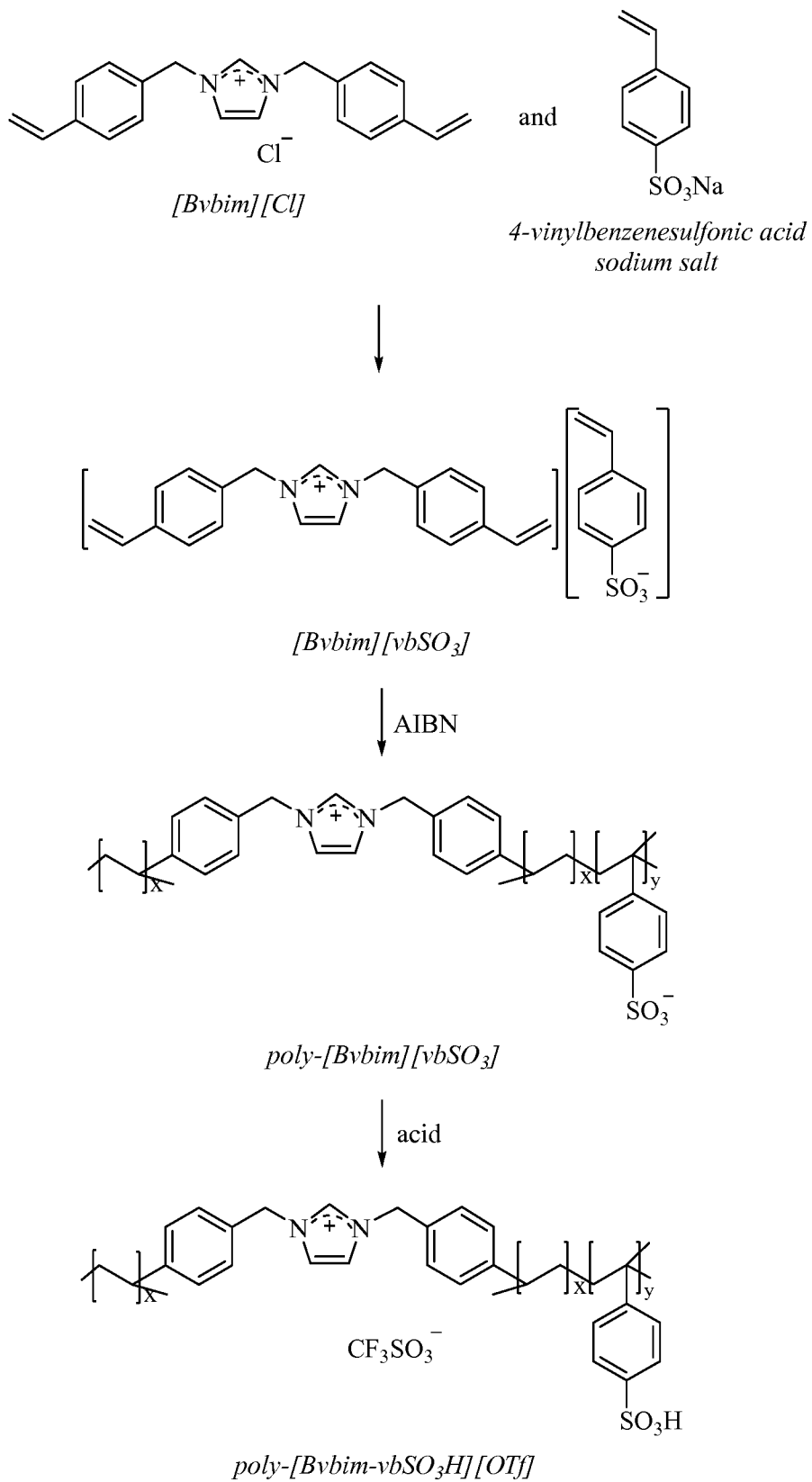
FIG. 3 shows a generalized scheme of the ionic polymer IP 3 preparation.

A generalized scheme of the ionic polymer IP 3 (poly[1,3-bi(4-vinylbenzylimidazolium)-co-4-vinylbenzylsulfonium][triflate]) preparation is shown in FIG. 3 and the details for each step are provided below.

Preparation of Bi-Vinylbenzene-Imidazolium Chloride ([Bvbint][Cl]):

A mixture of 1-trimethylsilylimidazole (0.100 mol) and chloromethylstyrene (0.242 mol) in dichloromethane (50 mL) was heated under reflux for 24 h. The solvent and trimethylsilyl chloride (Me3SiCl) was removed under reduced pressure and the remaining solid was washed with diethyl ether (3×15 mL) and dried under vacuum for 24 h.

Preparation of the Monomer [Bvbim][vbSO$_3$]:

A mixture of [Bvbim]Cl (0.1 mol) and 4-vinylbenzenesulfonic acid sodium salt (0.1 mol) was mixed at RT in $H_2O$ for 6 h. Afterwards, the reaction mixture was decanted with dichloromethane (3×20 ml), and the organic phase was combined from each time and dried in the rotar vap.

Preparation of the Polymer Poly-[Bvbim][vbSO$_3$]:

Monomer [Bvbim][vbSO$_3$] (1 g) was refluxed in 25 ml of ethanol/H$_2$O (4:1) mixture in presence of azobisisobutyronitrile (AIBN) (0.5 wt %) overnight, filtered and washed with diethyl ether.

Polymer Protonation Poly-[Bvbim-vbSO$_3$H][OTf]Poly[1,3-bi(4-Vinylbenzylimidazolium)-Co-4-Vinylbenzylsulfonium] [Triflate]:

Neutral polymer (1 g) and trifluoromethanesulfonic acid (CF□SO□OH) (0.32 g) were mixed together in 20 ml H$_2$O for 1 hour. Afterwards, the obtained acidic polymer was washed with diethyl ether (3*50 ml) and dried under vacuum overnight.

Synthesis of Other Ionic Polymers of the Invention

When above-mentioned 1-trimethylsilylimidazole is substituted with another cation A of formula (I) of the invention (see above), synthesis of alternative ionic polymers with different cations is achieved. The functionalization of cation can be performed following different approaches (see for example Chem. Rev., 2014, 114 (20), pp PR1PR70, DOI: 10.1021/cr500106x). As example, the traditional method for a functionalized imidazole is to reflux the mixture of diketones, bisaldehydes, and NH$_4$OAc in acetic acid for 5 hours (as shown below, see Chem. Rev., 2014, 114 (20), pp PR1PR70, DOI: 10.1021/cr500106x)

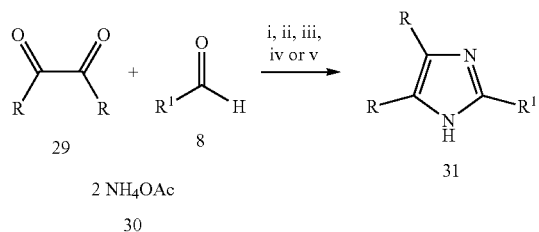

R=Ph
R$^1$=Ph, 4-F-Ph, 4-Cl-Ph, 2-Cl-Ph, 2,4-(Cl)$_2$-Ph, 4-NO$_2$-Ph, 4-OMe-Ph, 2-OMe-Ph, 4-(O—CH$_2$Ph)-Ph, 2-OH-Ph, 4-OH-3-OMe-Ph, 3-Cl-Ph, 3,4,5-(OMe)$_3$-Ph, Fur-2-yl, 3-OH-Ph, 3,4-(OMe)$_2$-Ph, 2,4-(OH)$_2$Ph, 4-CN-Ph, 4-CHO-Ph, 4-(CH(OEt)$_2$)-Ph, 2-OH, 3-Br-Ph, 4-(CHMe$_2$)-Ph, 2-OMe-Ph, Ph-4-OCH$_2$Ph, 3,5(OMe)$_2$, 4-OH-Ph, Naphth-1-yl, Antracen-1-yl, —CH=CHPh, —C(Me)=CHPh, —CH=CH-Ph-(4-NMe$_2$), —CH(Me)Ph, Bn, CH$_2$CH$_2$Ph, Hexyl, Octyl, 2-Br-Ph i: [HBIM][BF$_4$], 100° C., 25-120 min (85-98%).

It: [HeMIM][BF$_4$], MW, 135 W, 2-6 min (74-96%).

iii: TBAB, isopropanol, 82° C., 15-30 min (81-98%).

iv [HMIM][HSO$_4$], EtOH, 75° C., 2-8.5 h (79-97%).

v: [EMIM][Ac], EtOH,))), r.t., 45-90 min (70-96%).

The obtained product is followed by the silylation process to achieve a trimethylsilyl-functionalized organic compound. Additionally, a wide range of C2-substituted ionic monomers could be prepared via standard alkylation chemistry in the presence of a base (organic or inorganic) and the desired functional group (as shown below) (see Molecules 2009, 14(6), 2235-2245; doi:10.3390/molecules14062235):

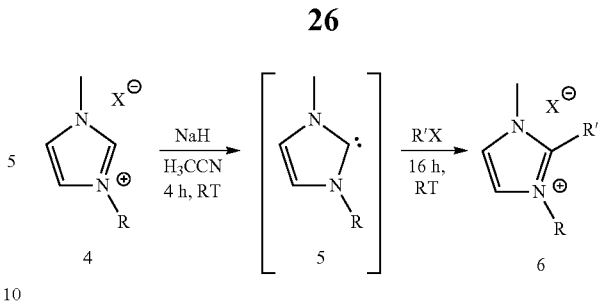

Cellulose Decomposition 30 mg of cellulose (preliminary ball-milled), 30 mg of the ionic polymer IP 2 (poly[1,3-bi(4-vinylbenzylimidazolium)-co-4-vinylbenzylsulfonium][hydrogen sulfate]) and 3 ml of H$_2$O were paced in a glass vial. The vial was sealed and the reaction mixture was then heated at 150° C. for 1 hour. After reaction the mixture was cooled to RT, diluted with water (10 ml) and filtered for further analysis. The residue was dried at 105° C. overnight (12 h) and solubilization of 93±2 wt % was determined including 26 wt % glucose and fructose (ratio 3 to 1).

Example of Polymer Recycling

A portion of the polymer recovered from above is returned to the glass vial. 30 mg of additional cellulose and 3 ml of H$_2$O are added, and the mixture is treated as above. Following the reaction, the reaction mixture can be separated, products recovered and the polymer reused multiple times.

Chitin hydrolysis High-value product d-glucosamine (GlcN) can be obtained from chitin in an excellent yield via co-solvent enhanced hydrolysis in presence of ionic polymers of the inventions (IPs). Final yield of 50-80% of GlcN can be achieved at 165-200° C. for 1-3 hours in a mixture of water-organic solvent depending on the added IPs.

Lipids Preparation 100 mg of spent coffee grounds (SCG), 30 mg of the ionic polymer IP 3 and 3 ml of H$_2$O were paced in a reactor. The reactor was sealed and the reaction mixture was then heated at 200° C. for 4 hours. After reaction, the mixture was cooled to RT, and 6 ml of hexane were added to the liquid fraction and the residual leftovers. After mixing for 1 hour the organic layer was collected and the hexane was evaporated. The concentrated lipids were dried and weighed and analysed. The obtained lipids are hexanedecanoic acid, oalmitic acid, octanedecanoic acid and stearic acid, that were identified as the main extracted products.

Additional catalysts and/or additional gases (CO$_2$ and/or H$_2$) may be used as well as a continuous extraction process of the product may be employed.

Spent Coffee Grounds (SCG) Decomposition (Specific Degree of Polymerization (DP))

Figure 4:
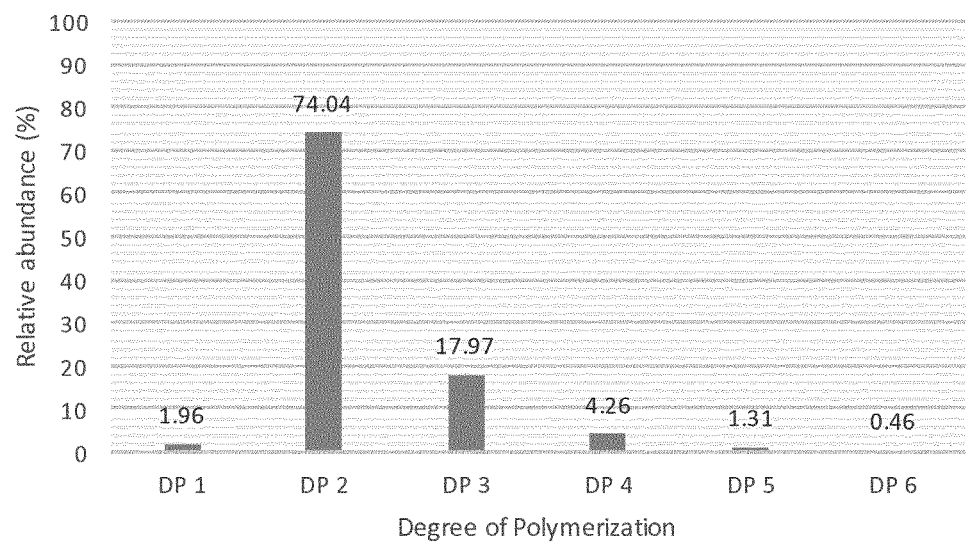
FIG. 4 shows oligosaccharide products distribution after SCG treatment with the ionic polymer IP 3 at 150° C. for 1 h. DP degree of polymerization.
Figure 5:
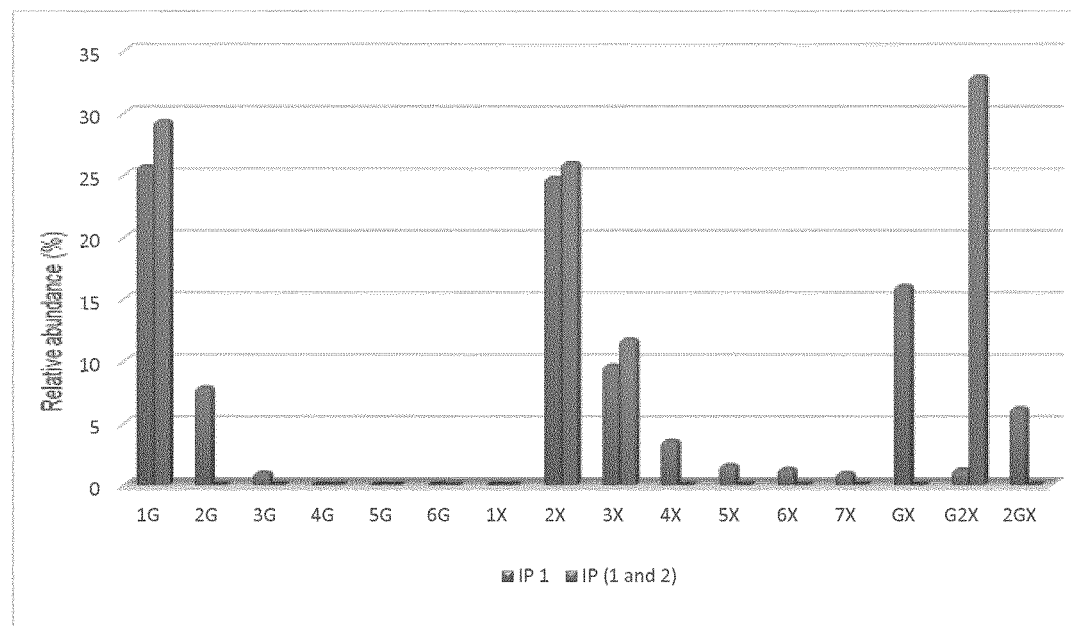
FIG. 5 shows oligosaccharide products distribution obtained from corncob after the reaction with IP 1 poly[1,3-bi(4-vinylbenzylimidazolium)-co-4-vinylbenzylsulfonium][chloride] and mixture IP 1 poly[1,3-bi(4-vinylbenzylimidazolium)-co-4-vinylbenzylsulfonium][chloride] with IP 2 poly[1,3-bi(4-vinylbenzylimidazolium)-co-4-vinylbenzylsulfonium][hydrogen sulfate]. G-glucose monomer, X-xylose monomer; number before G or X corresponds to the number of monomers in the chain.

100 mg SCG, 30 mg of the ionic polymer IP 3 and 3 ml of H$_2$O 2O were paced in a glass vial. The vial was sealed and the reaction mixture was then heated at 135° C. for 1 hour. After reaction the mixture was cooled to RT, diluted with water (10 ml) and filtered for further analysis. The residue was dried at 105° C. overnight and solubilization of 70±2 wt % was determined. When the reaction temperature was increased to 150° C. for 1 hour, 90±2 wt % were solubilized providing in both cases sugar oligo- and monosaccharides. The distribution of the final products in the form of oligo- and monosaccharides is shown in FIG. 4 (for SCG treated at 150° C.).

Corncob Transformation into Mono and Oligosaccharides 400 mg corn cob were mixed with 35 mg IP 1 (or 20 IP 1 and 15 IP 2 and 3 ml of water at 154° C. for 3 hours. After reaction, the mixture was cooled to RT, diluted with water (till 25 ml) and filtered for further analysis.

Ionic polymers mixture can be obtained either by physical mixing of each ionic polymer or by protonation reaction (last step in preparation) in a mixture of appropriate acids (for example HCl and $H_2SO_4$).

Production of Furanic Compounds (HMF and Furfural) from Corncob

HMF and furfural (yields of 25 and 75% respectively) can be obtained from corncob with IPs of the present invention in water as a solvent without any metal catalyst addition. To 250 mg corncob add 35 mg IP 3 and 10 ml $H_2O$. Mix at 200° C. for 4 h. Results: 25% HMF and 75% of furfural.

Production of Furanic Compounds from Sugars

Fructose to HMF or HMF/MMF can be obtained. To 300 mg of fructose add 100 mg of IP 3, 27 mg of $NH_4Cl$, 0.1 ml $H_2O$ 2O and 4 ml MeOH. Mix under 150° C. for 2 h. Results: 98% conversion, 25% yield of HMF, 37% yield of MMF and 20% methyl levulinate.

Figure 2:
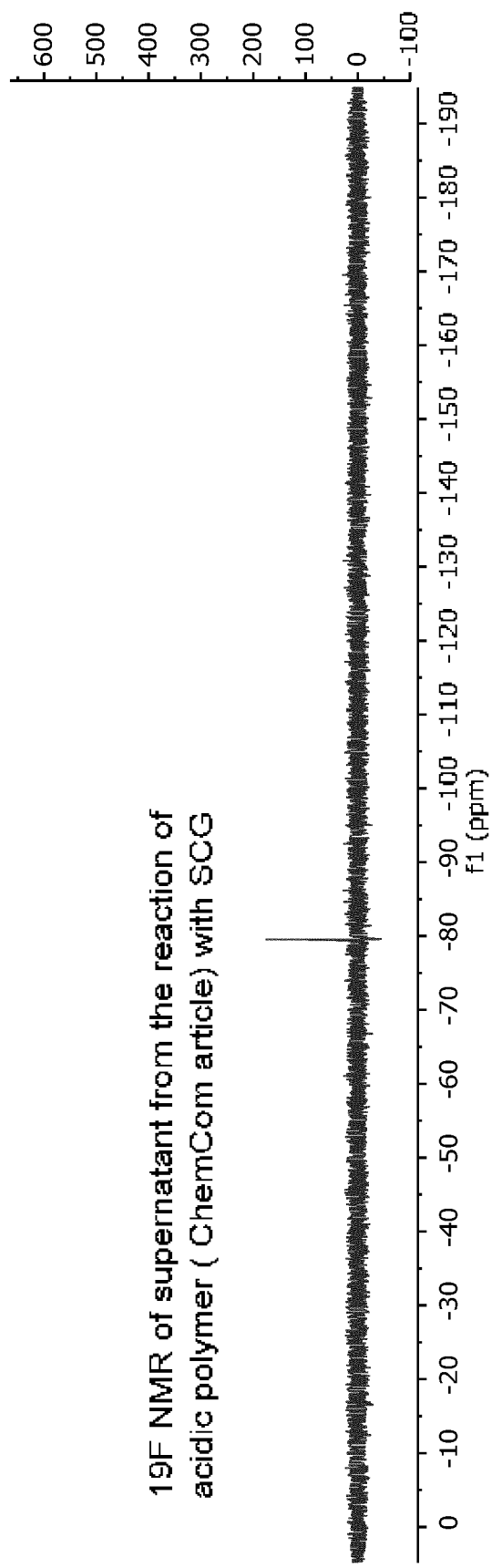
FIG. 2 shows 19F NMR spectra of reaction of polymer from Liu et al. with SCG (top) and of the disclosed polymer before (middle) and after reaction (bottom).

Leaching Test—Comparison of the Ionic Polymer Poly-[Bybim-vbSO$_3$H] [OTf] with Sponge-Like Polymers PDVB—SO$_3$H[C$_3$Vim][CF$_3$SO$_3$] of the Prior Art The leaching test was performed to determine the presence of the ionic polymer of the invention and the sponge-like polymers PDVBSOBH[C$_3$vim][CF$_3$SO$_3$] of the prior art in the reaction medium when these polymers were used to process biomass. The confirmation of leaching process in the reported polymers has been observed by 19F NMR. In the aqueous phase containing the product, that has been filtered, no ionic polymer of the invention was detected. When the sponge-like polymer of the prior art was tested, this polymer was detected in the product (see spectra in FIG. 2). As a result, application of the sponge-like polymer of the prior art is not possible for cases where leaching could contaminate and affect further treatment of the fractionation products (e.g. food grade products), as traces of triflate spill in the solution. In contrast to that, the ionic polymers of the invention do not show any presence of 19 F either before or after hydrolysis when used in processing of biomass, demonstrating its advantages for any practical applications.

The invention claimed is:

1. An ionic polymer (IP) of formula (I) consisting of anions and a polymeric backbone containing cations

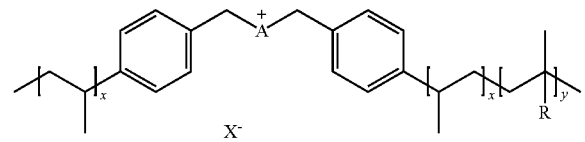

(I)

wherein

R is selected from substituted $C_1$-$C_{20}$ alkyl and substituted $C_5$-$C_{10}$ aryl, wherein substituents are selected from the group consisting of H, —SO$_3$H, —COOH, —[P(=O)(OH)$_2$], —[P(=O)(OH)],—O—SO$_3$H, —O—COOH, —O—[P(=O)(OH)$_2$] and —O—[P(=O)(OH)];

A is a cation selected from the group consisting of

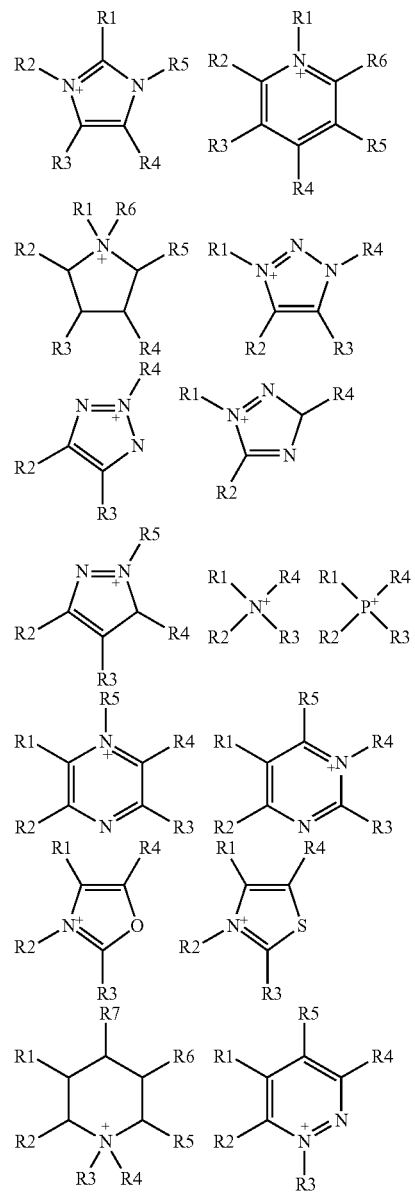

R1, R2, R3, R4, R5, R6 and R7 are each independently selected from the group consisting of a bond, H, $C_1$-$C_6$ alkyl, allyl, CH$_3$—(CH$_2$)n—O—(CH$_2$)m—CH$_3$, $C_1$-$C_6$ alkoxy, $C_1$-$C_6$ alkoxyalkyl, benzyl and —SO$_3$H, provided that two of R1, R2, R3, R4, R5, R6 and R7 are each a bond to the polymeric backbone;

n and m are independently selected from the group consisting of 0, 1, 2, 3, 4, 5 and 6;

x and y are integers each independently selected within the range 1 to 1000;

X is selected from the group consisting of F$^-$, Cl$^-$, Br$^-$, I$^-$, ClO$_4^-$, BF$_4^-$, PF$_6^-$, AsF$_6^-$, SbF$_6^-$, NO$_2^-$, NO$_3^-$, HSO$_4^-$, SO$_4^{2-}$, PO$_4^{3-}$, HPO$_4^{2-}$, CF$_3$CO$_2^-$, CF$_3$CO$_3^-$, CO$_3^{2-}$, CF$_3$SO$_3^-$, $C_1$-$C_6$ carboxylate, CN$^-$, SCN$^-$, OCN$^-$, CNO$^-$, N$_3^-$, tosylate, mesylate, trifluoromethanesulfonate, trifluoroethane sulfonate, di-trifluoromethanesulfonyl amino, docusate and xylenesulfonate.

2. The ionic polymer of claim 1, wherein R is substituted $C_6$ aryl and the substituents are selected from the group comprising consisting of H Z and —$SO_3H$.

3. The ionic polymer of claim 1 represented by formula

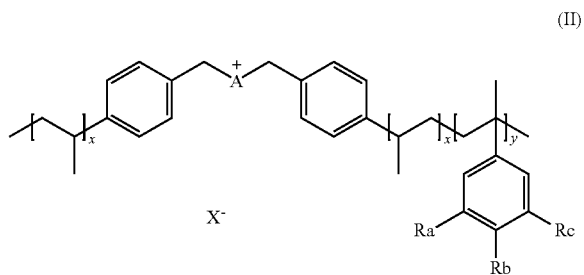

(II)

wherein
Ra, Rb, Rc are each independently selected from the group consisting of H, —$SO_3H$, —COOH, —[P(=O)(OH)$_2$], —[P(=O)(OH)], —O—$SO_3H$, —O—COOH, —O—[P(=O)(OH)$_2$], and —O—[P(=O)(OH)].

4. The ionic polymer of claim 1 represented by the following formula wherein X is 1P1, 1P2, or 1P3;

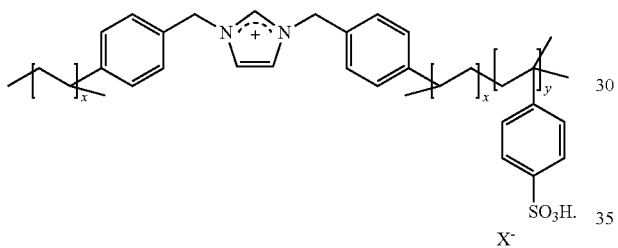

IP 1: X = Cl$^-$
IP 2: X = $HSO_4^-$
IP 3: X = $CF_3SO_3^-$

5. A solid support having at least one surface comprising one or more ionic polymers of claim 1.

6. A polymer membrane incorporating one or more ionic polymers of claim 1.

7. A method for producing one or more fine chemicals selected from the group consisting of lipids, sugars, furanic compounds and humins from biomass, the method comprising the steps of:
   a) providing biomass;
   b) optionally determining lipids and/or sugars contents in the biomass;
   c) optionally pretreating the biomass;
   d) contacting the biomass with a catalyst to form a reaction mixture, wherein the catalyst is an ionic polymer or a combination of ionic polymers of claim 1, a membrane incorporating the one or more ionic polymers of claim 1 or a solid support having at least one surface comprising one or more of the ionic polymers of claim 1;
   e) degrading the biomass in the reaction mixture to produce a liquid phase and a solid phase, wherein the liquid phase includes the one or more fine chemicals, and the solid phase includes residual biomass;
   f) isolating at least a portion of the liquid phase from the solid phase; and
   g) recovering the one or more fine chemicals from the isolated liquid phase.

8. The method of claim 7, wherein the step d) comprises adding an appropriate water or organic solvent and an effective amount of the catalyst to the biomass to form a reaction mixture, and degrading step e) comprises heating the reaction mixture of step d) during appropriate time and subsequently cooling to room temperature.

9. The method of claim 8, wherein the organic solvent is selected from the group consisting of alcohol, ether, ketone, DMSO, DME, DMF, THF and ionic liquids.

10. The method of claim 8, wherein the heating temperature is held at a maximum of 250° C.

11. The method of claim 7, wherein recovering the one or more fine chemicals can be done by filtration, centrifugation or gravity settling.

12. The method of claim 7, wherein the optional pretreatment of the biomass is carried out and uses one or more pretreatment methods selected from the group consisting of washing, solvent-extraction, solvent-swelling, comminution, milling, steam pretreatment, explosive steam pretreatment, dilute acid pretreatment, hot water pretreatment, alkaline pretreatment, lime pretreatment, wet oxidation, wet explosion, ammonia fiber explosion, organosolvent pretreatment, biological pretreatment, ammonia percolation, ultrasound, electroporation, microwave, supercritical $CO_2$, supercritical $H_2O$, ozone, and gamma irradiation.

13. The method of claim 7, wherein the biomass is selected from the group consisting of cellulosic, chitinous, oleaginous and lignocellulosic material.

14. A method for producing C5 and C6 sugars, furfural, 5-hydroxymethylfurfural (HMF) and derivatives of HMF from biomass, the method comprising the steps of:
   a) providing biomass;
   b) optionally determining sugars contents in the biomass;
   c) optionally pretreating the biomass;
   d) contacting the biomass with a catalyst to form a reaction mixture, wherein the catalyst is an ionic polymer or a combination of ionic polymers of claim 1, a membrane incorporating the one or more ionic polymers of claim 1 or a solid support having at least one surface comprising one or more of the ionic polymers of claim 1;
   e) degrading the biomass in the reaction mixture to produce a first liquid phase and a first solid phase, wherein the first liquid phase includes C5 oligomer sugars and/or C5 monomer sugars and can further include furfural if the time of degrading step is extended, and the first solid phase includes residual material;
   f) isolating at least a portion of the first liquid phase from the first solid phase;
   g) recovering C5 oligomer sugars and/or C5 monomer sugars and/or furfural from the isolated first liquid phase;
   h) contacting the first solid phase that includes residual material with the same catalyst as in step d) or with a different catalyst, to form a reaction mixture, wherein the catalyst is the ionic polymer or a combination of the ionic polymers, a membrane incorporating the one or more ionic polymers or a solid support having at least one i) further degrading the first solid phase that includes residual material in the reaction mixture to produce a second liquid phase and a second solid phase, wherein the second liquid phase includes C6 oligomer sugars and/or C6 monomer sugars and can further include 5-hydroxymethylfurfural (HMF) and derivatives of HMF and/or humins if the time of degrading step is extended, and the second solid phase includes residual material;

j) isolating at least a portion of the second liquid phase from the second solid phase; and k) recovering C6 oligomer sugars and/or C6 monomer sugars and/or 5-hydroxymethylfurfural (HMF) and derivatives of HMF and/or humins from the isolated second liquid phase.

15. The method of claim 14, wherein the step d) comprises adding an appropriate water or organic solvent and an effective amount of the catalyst to the biomass to form a reaction mixture, and degrading steps e) and i) comprises heating the reaction mixture during appropriate time and subsequently cooling to room temperature.

* * * * *

UNITED STATES PATENT AND TRADEMARK OFFICE
CERTIFICATE OF CORRECTION

PATENT NO.        : 10,894,851 B2
APPLICATION NO.   : 16/085809
DATED             : January 19, 2021
INVENTOR(S)       : Paul Dyson et al.

It is certified that error appears in the above-identified patent and that said Letters Patent is hereby corrected as shown below:

In the Claims

At Column 29, Claim number 2, Line 3, "comprising consisting of H Z and $-SO_3H$." should be changed to --consisting of H and $-SO_3H$.--

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*